United States Patent
Groscurth et al.

(10) Patent No.: US 10,363,115 B2
(45) Date of Patent: Jul. 30, 2019

(54) METHOD OF USING AN ENDENTULOUS SURGICAL GUIDE

(71) Applicants: Randall C. Groscurth, Troy, MI (US); Shoko U. Groscurth, Troy, MI (US)

(72) Inventors: Randall C. Groscurth, Troy, MI (US); Shoko U. Groscurth, Troy, MI (US)

(73) Assignee: IBUR, LLC, Troy, MI (US)

(*) Notice: Subject to any disclaimer, the term of this patent is extended or adjusted under 35 U.S.C. 154(b) by 60 days.

(21) Appl. No.: 15/401,917

(22) Filed: Jan. 9, 2017

(65) Prior Publication Data
US 2017/0112592 A1   Apr. 27, 2017

Related U.S. Application Data

(63) Continuation-in-part of application No. 15/359,167, filed on Nov. 22, 2016, now Pat. No. 10,034,722.
(Continued)

(51) Int. Cl.
A61C 13/00 (2006.01)
A61C 8/00 (2006.01)
(Continued)

(52) U.S. Cl.
CPC ............ *A61C 1/084* (2013.01); *A61B 5/4547* (2013.01); *A61B 6/032* (2013.01); *A61B 6/14* (2013.01);
(Continued)

(58) Field of Classification Search
CPC ... A61C 13/0004; A61C 8/0089; A61C 7/002; G06T 17/00; G06T 19/20; G06T 2210/41
See application file for complete search history.

(56) References Cited

U.S. PATENT DOCUMENTS

4,998,881 A   3/1991   Lauks
5,857,853 A   1/1999   van Nifterick et al.
(Continued)

FOREIGN PATENT DOCUMENTS

EP   0328911 A2   8/1989
EP   1502556 A2   2/2005
(Continued)

OTHER PUBLICATIONS

English abstract for EP2425796.
(Continued)

*Primary Examiner* — Utpal D Shah
(74) *Attorney, Agent, or Firm* — Fishman Stewart PLLC

(57) ABSTRACT

An approach is disclosed that involves creating an updated master dental model of a patient's mouth after an implant surgery by aligning new postoperative oral scan data to pre-existing preoperative oral scan data that is more comprehensive (e.g., it includes bite registration). Before surgery a multi-piece stackable surgical guide set is created using the preoperative oral scan data. The surgical guide set is used to facilitate the surgery. After the surgery at least one piece of the surgical guide set is placed back in a patient's mouth and may act as a reference marker because it was created using the preoperative oral scan data, but is also part of the postoperative mouth configuration since it was used to facilitate the surgery. The affected portion of the mouth may then be digitally scanned directly or indirectly by way of a physical impression with the reference marker in place to determine the new characteristics resulting from the surgery such as new implant installation locations and orientations. The new postoperative oral scan data may be combined with the pre-existing preoperative oral scan data by way of the reference marker (since it is a constant between the two sets of scan data) without having to do such things as take a new (Continued)

bite registration, on which a new implant restoration can be easily created.

19 Claims, 20 Drawing Sheets

Related U.S. Application Data which is a continuation of application No. 13/621,146, filed on Sep. 15, 2012, now Pat. No. 9,504,533.

(60) Provisional application No. 61/535,698, filed on Sep. 16, 2011, provisional application No. 62/276,083, filed on Jan. 7, 2016.

(51) Int. Cl.

| | | |
|---|---|---|
| *G06T 19/20* | (2011.01) | |
| *G06T 17/00* | (2006.01) | |
| *A61C 1/08* | (2006.01) | |
| *A61B 6/03* | (2006.01) | |
| *A61B 6/14* | (2006.01) | |
| *A61C 9/00* | (2006.01) | |
| *A61C 13/34* | (2006.01) | |
| *A61B 6/00* | (2006.01) | |
| *A61B 90/00* | (2016.01) | |
| *A61C 13/107* | (2006.01) | |
| *A61C 19/05* | (2006.01) | |
| *A61B 5/00* | (2006.01) | |
| *B33Y 80/00* | (2015.01) | |

(52) U.S. Cl.
CPC .......... *A61B 6/4085* (2013.01); *A61B 6/5229* (2013.01); *A61B 90/39* (2016.02); *A61C 8/0089* (2013.01); *A61C 9/004* (2013.01); *A61C 13/0001* (2013.01); *A61C 13/0004* (2013.01); *A61C 13/34* (2013.01); *A61C 19/05* (2013.01); *G06T 17/00* (2013.01); *G06T 19/20* (2013.01); *B33Y 80/00* (2014.12)

(56) References Cited

U.S. PATENT DOCUMENTS

| | | | |
|---|---|---|---|
| 6,672,870 B2 | 1/2004 | Knapp | |
| 8,926,328 B2 * | 1/2015 | Suttin | A61C 8/0001 |
| | | | 433/213 |
| 9,375,297 B2 * | 6/2016 | Davison | A61C 5/007 |
| 10,206,757 B2 * | 2/2019 | Pettersson | A61C 1/084 |
| 2008/0166681 A1 * | 7/2008 | Weinstein | A61C 1/084 |
| | | | 433/76 |
| 2009/0011382 A1 | 1/2009 | Bavar | |
| 2009/0298009 A1 | 12/2009 | Brajnovic | |
| 2010/0075275 A1 | 3/2010 | Brajnovic | |
| 2010/0124731 A1 * | 5/2010 | Groscurth | A61C 9/00 |
| | | | 433/213 |
| 2010/0190137 A1 | 7/2010 | Hertz | |
| 2010/0203479 A1 | 8/2010 | Bulloch et al. | |
| 2010/0256649 A1 | 10/2010 | Capsal et al. | |
| 2011/0045431 A1 * | 2/2011 | Groscurth | A61C 1/084 |
| | | | 433/74 |
| 2011/0045432 A1 * | 2/2011 | Groscurth | A61C 1/084 |
| | | | 433/75 |
| 2011/0054656 A1 * | 3/2011 | Lee | G06T 3/0068 |
| | | | 700/98 |
| 2011/0217667 A1 * | 9/2011 | Groscurth | A61C 9/004 |
| | | | 433/68 |
| 2012/0046914 A1 * | 2/2012 | Gao | A61C 1/084 |
| | | | 703/1 |
| 2013/0172731 A1 * | 7/2013 | Gole | A61B 5/0035 |
| | | | 600/424 |
| 2014/0272778 A1 * | 9/2014 | Llop | A61C 8/0089 |
| | | | 433/72 |
| 2015/0010881 A1 * | 1/2015 | Llop | A61C 1/084 |
| | | | 433/75 |
| 2016/0157964 A1 * | 6/2016 | Suttin | A61C 8/0089 |
| | | | 433/27 |
| 2016/0354169 A1 * | 12/2016 | Suttin | A61B 34/30 |

FOREIGN PATENT DOCUMENTS

| | | |
|---|---|---|
| EP | 2425796 A1 | 3/2012 |
| WO | WO-2009/115617 A1 | 9/2009 |

OTHER PUBLICATIONS

English abstract for EP1502556.
International Search Report for PCT/US2012/055684, dated Nov. 23, 2012.
Patzelt, S.B.M., Emmanouilidi, A., Stampf, S. et al. "Accuracy of full-arch scans using intraoral scanners" Clin Oral Invest (2014) 18: 1687. doi:10.1007/s00784-013-1132-y.

* cited by examiner

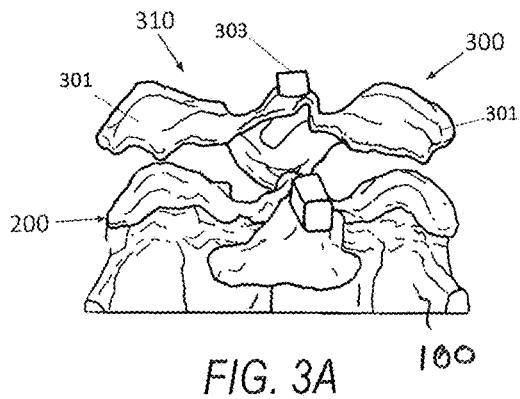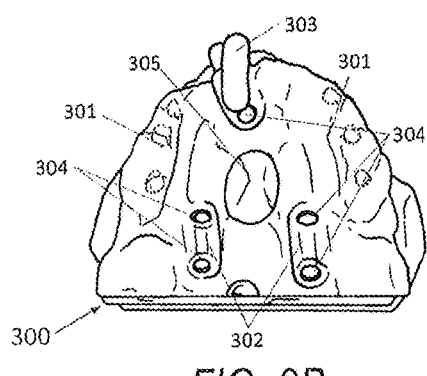
FIG. 3A   FIG. 3B
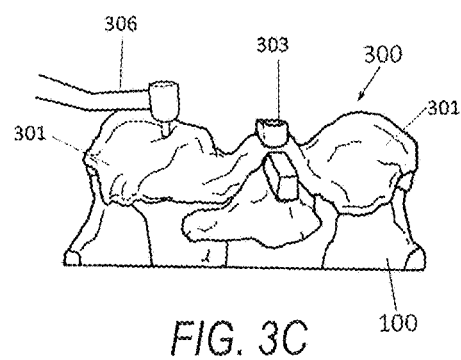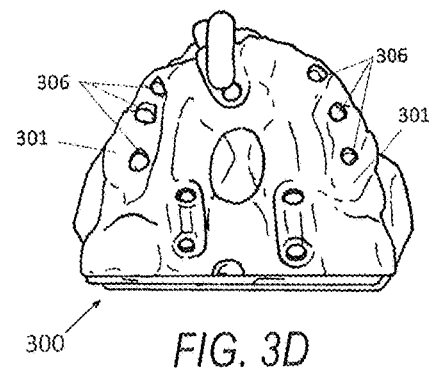
FIG. 3C   FIG. 3D
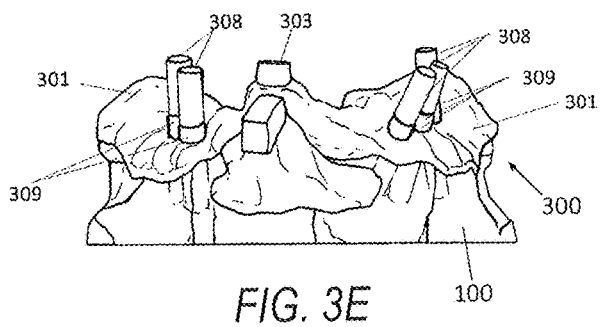
FIG. 3E

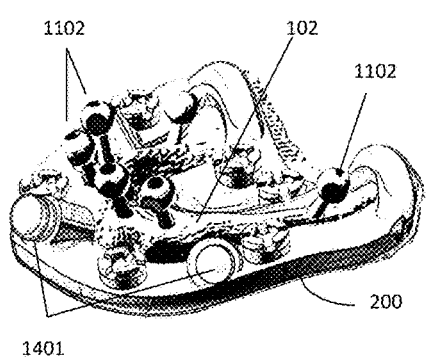
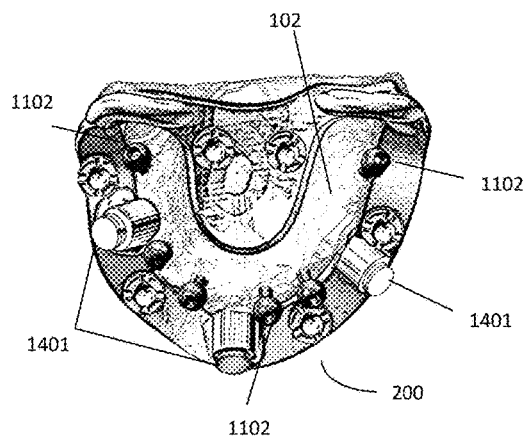
FIG. 19A
FIG. 19B
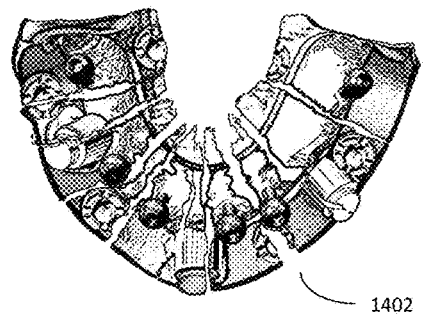
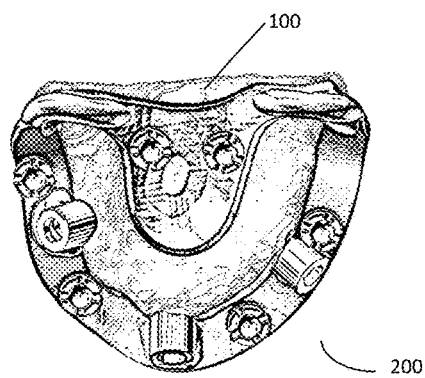
FIG. 19C
FIG. 19D
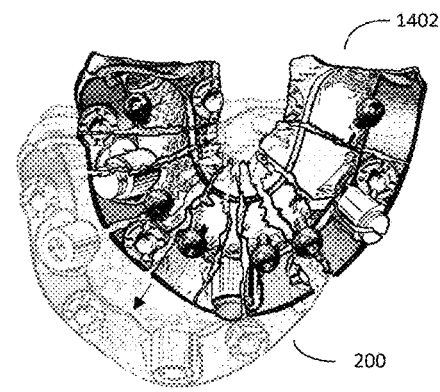
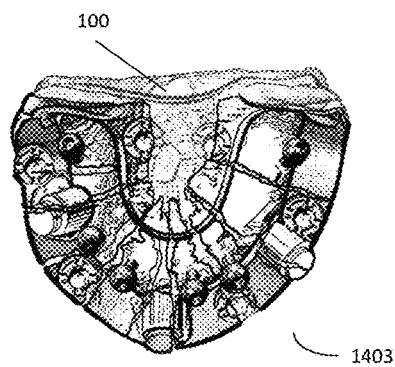
FIG. 19E

METHOD OF USING AN ENDENTULOUS SURGICAL GUIDE

CROSS-REFERENCE TO RELATED APPLICATIONS

This application is a continuation in part application of U.S. patent application Ser. No. 15/359,167, filed on Nov. 22, 2016, which is a continuation application of U.S. patent application Ser. No. 13/621,146, filed on Sep. 15, 2012, which claims priority to U.S. Provisional Application No. 61/535,698, filed on Sep. 16, 2011. This application also claims priority to U.S. Provisional Patent Application No. 62/276,083, filed on Jan. 7, 2016. The contents of all of these applications is hereby incorporated by reference in their entirety.

FIELD OF THE INVENTION

An improved dental implant method and apparatus is disclosed, and, more particularly, a surgical guide that can be fit to a patient's jawbone.

BACKGROUND AND SUMMARY OF THE INVENTION

Dental implants are commonly used in today's dental practices to support various prostheses. Challenges to the successful placement of dental implants include poor bone quality and various hidden anatomical features such as nerves, roots, and sinus cavities. Surgical preplanning methods and drill guide apparatuses may be used to better address these challenges. With edentulous cases, surgical drill guide apparatuses can be divided into two categories: bone borne surgical drill guides and gum tissue borne surgical guides.

Bone borne surgical drill guides are made to fit on a patient's jawbone, and can be made from either a digital jawbone model or rapid-prototyped physical jawbone model of the patient. The primary problem with bone borne surgical guides is the invasiveness of the amount of flapping of the gum tissue that the surgeon has to create in order for the guide to fit correctly on the patient jawbone. The amount of flapping required increases the likelihood of surgical risks and complications, including blood loss, infection, healing problems, and overall pain experienced by the patient. Flapping and suturing also requires a great deal of surgical time. In addition to the problems associated with the surgical procedure, difficulties may also arise when the jawbone has low density, which happens often with Maxilla bones in posterior region. Low bone density makes it difficult to define the contour of the bone in CT images, which may cause the bone borne surgical drill guide to fit poorly. Thus, the use of bone borne surgical drill guides has drawbacks and it would be preferred to overcome their associated problems.

Gum tissue borne surgical drill guides are made to fit on top of a patient's gum tissue without the need for any surgical incisions to stabilize the guide. In order to create this type of surgical guide, the surface scan data of the gum tissue and the tomography data of the jawbone need to be accurately aligned and mapped. For this purpose, usually an imaging template is worn by the patient during tomography scanning, and the fiducial markers on the device are used for alignment of the different data sets. While this method is less surgically invasive than the bone borne method, gum tissue borne surgical guides lack stability. Gum tissue is in a constant state of movement and drift, and is also pliable with pressure. Moreover, certain health conditions and even the intake of certain foods make gum tissue more prone to swelling. These conditions may prevent the accurate positioning of the device in the mouth. Here, even if the surgeon uses anchor screws, they may be securing the device in the wrong position. This type of surgical drill guide sacrifices accuracy for convenience. Thus, it would be preferred to overcome these problems.

Accordingly, it would be desirable to provide a stable and accurate surgical drill guide apparatus that requires only minimum flapping and fits to both gum tissue and one or multiple small areas of jawbone. Such apparatus may increase the stability of the surgical guide by clasping and/or contacting the jawbone, while improving the overall fit and minimizing the need of flapping by also clasping and/or contacting selected areas of the gum tissue at the same time. The apparatus may be configured to accurately place dental implants according to the planned positions.

It would also be preferable to provide an apparatus that may be custom designed to suit the unique anatomical features of each individual. The device may be designed on a digital anatomical jawbone model with accurately mapped and aligned gum tissue information, and may be rapid prototyped or milled as a drill guide frame or frame set. Also, the apparatus may be made by hand on the rapid prototyped or CNC milled physical anatomical model that partially exposes the jawbone structure.

Currently, the most common way of taking a positional index of installed implants is by taking a dental impression. Right after the placement of implants or after the integration of implants, impression copings are placed on the installed implants and a dental impression is taken using an impression tray and one or more dental impression materials. For more accuracy with fully edentulous cases with multiple implants, it is recommended that the impression copings are splinted with some rigid materials before the impression is taken. Then a new master dental model is created from the impression in a traditional way, using implant analogs. Because of the stress applied on the impression copings and material distortion by the impression materials and impression tray, a verification jig should be made to verify the model and, if the gum tissue contour is altered, a new impression will be taken after it is healed. Alternatively, instead of a physical impression, the positions of installed implants may be recorded by surface scanning the patient's mouth with an intraoral scanner, and a new master dental model can be produced by rapid prototyping.

However, with either method, if the contour of the gum tissue is altered by dentition extraction, bone adjustment, or bone grafting, preoperative information such as the bite registration, existing prosthesis, and natural dentition before extraction, can no longer be used in order to articulate the new master dental model to the opposing jaw model. This is the case with a majority of edentulous flap surgeries, and, if so, the dental practitioner must go through another cumbersome set of procedures of taking a new bite registration since the information is essential for creation of a new prosthesis. This will most likely cause multiple adjustments back and forth between the dental practitioner and the dental laboratory because creating a full mouth prosthesis without the previous bite information can be a very difficult task once the information is lost. The teachings herein help to solve these and other problems.

Preoperative Data File and Creation of Guide Appliances

According to an illustrative approach, the master data file may be created with the data sets incorporating one or more surface and/or tomography scans of a patient's mouth, digital topography data of the patient's existing fixed or removable prosthesis, digital topography data of the dental impression, digital topography data of the dental cast, and other related preoperative information such as bite registration, oriented to each other with coordinates defined by at least one natural or artificial reference marker that exists under and is both fixed constant between the data sets. A natural reference marker refers to a pre-existing oral structure while an artificial reference marker refers to a marker inserted into a patient's mouth, but consistently fixed at the same coordinate location within the mouth after each insertion. In either case, for a reference marker its coordinates are consistent and do not change between scannings. A digital dental anatomical diagnostic model such as a digital preoperative master dental model (the 'digital preoperative model') may be created using the data in the master data file, and a multiple-piece stackable surgical guide set (the 'surgical guide set') may be designed using this digital preoperative model. Then the design of the surgical guide set is stored within the master data file and all the sections of the surgical guide set can be manufactured by rapid prototyping. The surgical guide set may include a base frame and one or more attachable/detachable superstructures such as a surgical drill guide section, transfer appliance section and temporary prosthesis section. There are mainly two different ways of taking a positional index of installed implants back to the preoperative model although there are many variations within these processes. One way is to take a digital positional index of installed implants and the other way is to take a physical positional index of installed implants. Both processes use a section of the surgical guide to connect the new information to the preoperative information.

Process of Taking a Digital Positional Index of the Installed Implants

If a dental practitioner chooses to take a digital positional index of the newly installed implants with an intraoral scanner, the base frame of the above surgical guide set can be utilized as a fiducial marker linkable to the digital preoperative model. After placement of dental implants represented in part by a fixed implant head extending outwardly from a body surface within a patient's mouth to hold various implant components, the surgical guide section may be removed from the base frame but the base frame will remain in the mouth. The base frame has a wide enough opening around the area of surgical sites so that the implant heads of dental implants are visible but not touching the base frame. Utilizing an intraoral scanner, the base frame may be scanned along with the implant heads. Now, the implant heads are indexed to the base frame within the scan data. The scan data can be then superimposed onto the digital preoperative model in the master data file by aligning the base frame portion of the scan data to the design of the base frame inside of the master data file already oriented to the digital preoperative model. The position of the installed implant heads, which are oriented to the base frame within the intraoral scan data, will be oriented to the digital preoperative model as well by this alignment, creating a digital postoperative dental model with installed implants' positions and angulations.

If a required implant head is not visible enough above the patient's oral structure, corresponding implant components such as a scan body, impression coping, and temporary abutment may be placed on the implants during the postoperative scan. Just like the currently used digital impression method, this method will allow the surgeon to take an index of the installed implants without applying physical stress on the implants or worrying about impression materials getting underneath the open gum tissue, but, unlike the currently used method, this method allows the dental practitioners and lab technicians to transfer the positional information of installed implants back to the digital preoperative model, to which other essential preoperative information may have been already oriented.

Process of Taking a Physical Positional Index of the Installed Implants

If a dental practitioner chooses to take a physical positional index of the patient's mouth, a superstructure of the surgical guide set can be utilized as a transfer jig. The superstructure that can be used as a transfer jig may include a specifically designed transfer jig appliance, a temporary prosthesis, and a surgical guide section. At the surgery, after a dental implant(s) are installed, corresponding implant components can be connected to the head of the installed dental implant; the implant head is usually the only visible portion of an implant and implant components are generally attached only to the head of the implant. Then the implant component may in turn be fixated to the superstructure used as a transfer jig by an adhesive material. If a transfer jig appliance (or temporary prosthesis) is used to take a physical positional index, the surgical guide can be removed from the base frame after installing implants and transfer jig appliance can be attached to the base frame and then connected to the implant components. Once this is done, the implant components can be detached from the implant heads with the superstructure (used as a transfer jig appliance) and base frame then removed from the mouth. Subsequently, the installed implants' positional information captured by the transfer attachment or the surgical guide section can be transferred back to either a digital or physical preoperative model, also called anatomical diagnostic models herein, in order to convert the preoperative model into the postoperative dental model taking into account the actual position of installed dental implant.

If the information is to be transferred to the digital preoperative model, the corresponding implant components attached to the transfer appliance (a superstructure used as a transfer jig) can be surface scanned either with a desktop surface scanner or hand held surface scanner. Now, the scan data contains the implant components indexed to the transfer appliance. The scan data can be then superimposed onto the digital preoperative model in the master data file by aligning the superstructure portion of the scan data to the design of the superstructure inside of the master data file already oriented to the digital preoperative model. The position of the implant components will be oriented to the digital preoperative model as well by this alignment, creating a digital postoperative dental model with installed implants' positions and angulations.

Alternatively, a physical preoperative model can be manufactured from the digital preoperative model by rapid prototyping and positional information of the installed dental implants can be transferred to the physical model by placing the surgical guide set along with the attached impression copings on the physical model.

As the base frame remains in the set position before and after the placement of implants at the surgery, all the superstructures including a transfer attachment will retain the same orientation as they were designed on the preoperative model. Thus, the information obtained by this method is transferable back to the physical or digital preoperative model. Additionally, if this method is used, the surgeon can save time on splinting the implants, and does not have to use an impression material to capture the impression of surrounding gum tissue along with the impression copings since the preoperative model has the all the obtainable information already. This will significantly reduce stress on the impression copings and connected implants.

Overview of the Two Illustrative Approaches of Combining the Postoperative Data Files and the Preoperative Data Files and Some of their Advantages The illustrative approaches have significant advantages over conventional teachings. For example, by using a section of the surgical guide set, a postoperative positional index of installed implants will become transferrable and linkable to the digital or physical preoperative model. Since all sections of the surgical guide set are created on the digital preoperative model within the master data file and the design of each section is stored with coordinates to the digital preoperative model, the scan image of each section can be perfectly aligned with its design already oriented to the digital model. Additionally, if a physical preoperative model is manufactured from the digital preoperative model, the implant components attached to a transfer attachment can be transferrable to the physical preoperative model because the surgical guide set is designed to fit both the patient's mouth and the preoperative model. This way, dental practitioners and lab technicians will be able to make full use of other preoperative information oriented to the digital or physical preoperative model, sparing them from time and trouble to re-obtain critical information, such as the bite registration and a contour of an ideal prosthesis. By bridging the preoperative information and postoperative information, a seamless workflow from the surgery to fabrication of a prosthesis is established. Taking a positional index of installed implants and creating the postoperative master model are much easier, and a new implant prosthesis can be created without numerous adjustments that may be required using conventional teachings.

BRIEF DESCRIPTION OF THE DRAWINGS

Referring now to the discussion that follows and also to the drawings, illustrative approaches are shown in detail. Although the drawings represent some possible approaches, the drawings are not necessarily to scale and certain features may be exaggerated, removed, or partially sectioned to better illustrate and explain the present disclosure. It should be noted that, although all the drawings presented here are of fully edentulous cases, the disclosed approaches are applicable to partially edentulous cases. Further, the descriptions set forth herein are not intended to be exhaustive or otherwise limit or restrict the claims to the precise forms and configurations shown in the drawings and disclosed in the following detailed description.

FIG. 3A is a side view of the exemplary drill guide housing frame for the upper jaw about to be attached to the exemplary base frame on the anatomical model;

FIG. 3B is a top view of the FIG. 3A drill guide housing frame, with skirted area on the base frame and the physical anatomical diagnostic model;

FIG. 3C is a side view of the FIG. 3A drill guide housing frame, with a hand piece drilling holes into the skirted areas;

FIG. 3D is a top view of the FIG. 3A exemplary drill guide housing frame, with holes that correspond with planned osteotomies on the physical anatomical diagnostic model;

FIG. 3E is a side view of the FIG. 3D physical anatomical diagnostic model, with positioning pins and drill guide bushings placed into the planned osteotomies through the holes on the skirt portion of the drill guide housing frame;

FIG. 16B-2 is an expanded bottom perspective view of another exemplary base frame and temporary prosthesis with connecting implant components;

FIG. 18D-1 is a simplified drawing of an intraoral scanner taking a digital impression of the patient's lower jaw with implant components attached on the installed implants after implant placement;

FIG. 18D-2 is a partial top view of the base frame of the multiple piece surgical guide set and the installed implant heads on the patient's lower jaw;

FIG. 18E-1 is a partial top view of the base frame of the multiple piece surgical guide set configured to receive additional attachment(s) and placed on the patient lower jaw along with the implant components attached to the installed implants;

FIG. 18E-2 is a partial top view of one design of additional superstructure (attachment) attached to the base frame placed on the patient's lower jaw with the implant;

FIG. 18E-3 is a partial top view of another design of additional attachments attached to the base frame placed on the patient's lower jaw with the implant components attached to the installed implants;

FIG. 19A is a top view of the digital design of another exemplary base frame;

FIG. 19B is a perspective view of the manufactured based frame positioned in a patient's mouth and implant components attached on the installed implants;

FIG. 19C is a top view of the manufactured based frame positioned in a patient's mouth and implant components attached on the installed implants;

FIG. 19D is an illustration showing how sections of scanned images by an intraoral scanner are digitally combined to create a whole image of the oral surface with the base frame and implant components positioned in the patient's mouth;

FIG. 19E is an illustration showing how distortion of scanned image by an intraoral scanner can be adjusted by aligning the image to the digital design of the base frame;

DETAILED DESCRIPTION

Figure 1A:
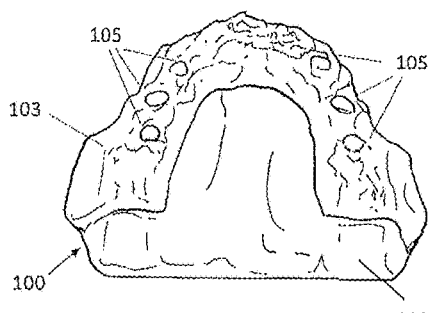
FIG. 1A is a top view of an upper jaw anatomical diagnostic model with gum tissue and a partially exposed bone structure.
Figure 1B:
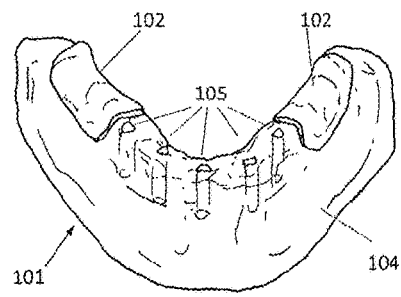
FIG. 1B is a perspective front view of a lower jaw anatomical diagnostic model with gum tissue and a partially exposed bone structure.

FIGS. 1A and 1B illustrate patient specific digital or physical dental anatomical diagnostic models 100 and 101 that expose the partial upper jawbone bone structures 103 and a lower jawbone 104 at the surgical sites and the areas of interest. In areas where the bone structures are not exposed, the model has gum tissue surface structures 102. As in FIGS. 1A and 1B, these gum tissue surface structures 102 usually appear towards the distal end of the posterior regions and the palatal area of the upper jaws.

Figure 1C:
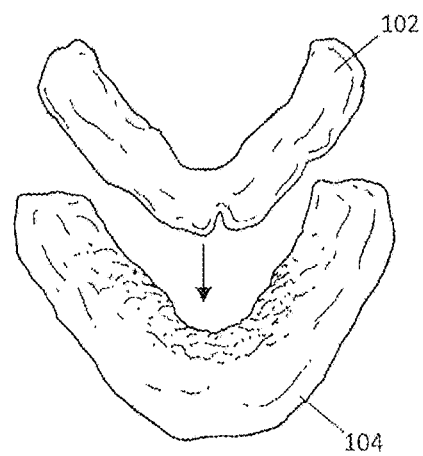
FIG. 1C is a perspective front view of a lower jawbone digital image and a gum tissue image which are about to be aligned.
Figure 1D:
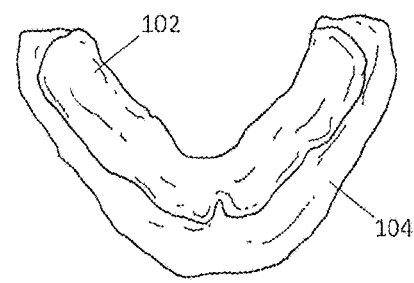
FIG. 1D is a perspective front view of a lower jaw bone digital image aligned with the gum tissue digital image.

FIGS. 1C and 1D depict a digital image of a lower jawbone 104 and a digital image of the gum tissue surface structures 102 positioned relative to one another, from which diagnostic anatomical models like 1A and 1B are created.

The bone structure data can be obtained by tomography imaging devices such as CT and CB CT, and may be exported as a file format, such as STL, suitable for reverse engineering and 3D imaging. Then the data file can be accurately aligned with the surface scan data of the gum tissue 102 obtained by devices such as laser and optical scanners by means of matching fiducial markers on the imaging apparatus that the patient wears during the tomography scan to the markers' positional information on the surface scan data. If the bottom of the apparatus represents the patient's gum tissue surface, the image of the patient's gum surface can also be obtained by scanning the imaging apparatus alone using a tomography device. In this case, these two CT data files can be aligned by the fiducial marker location(s) after each structure is thresholded and is exported as a proper file format for modeling. If a radio opaque duplicated denture is used as an imaging apparatus, the bone structure data and the gum surface data can be obtained with a single CT scan of the patient with the imaging apparatus in place. After the necessary structures are properly aligned in a file format suitable for 3D modeling, the data files can be combined and used to design a digital anatomical diagnostic model with a partially exposed bone structure in the area of the surgical site.

The osteotomies of simulated dental implant placements 105 may be created either digitally on the digital anatomical diagnostic model or manually on the rapid-prototyped physical anatomical diagnostic model. Then a drill guide apparatus may be designed on this type of digital anatomical diagnostic model so that it will accommodate drill guide bushings or holes which guide the surgical drill according to the planned osteotomies either on the digital anatomical diagnostic model or the physical anatomical diagnostic model. Alternatively, the whole apparatus can be designed manually on this type of physical anatomical diagnostic model with dental materials such as, but not limited to, light cured composite, cold cured resin or acrylic, or thermoplastic.

Figure 2A:
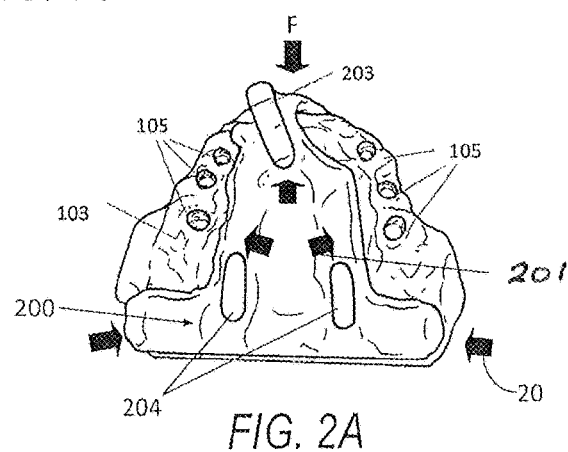
FIG. 2A is a top view of an exemplary base frame for an upper jaw on a diagnostic model with gum tissue and a partially exposed bone structure.
Figure 2B:
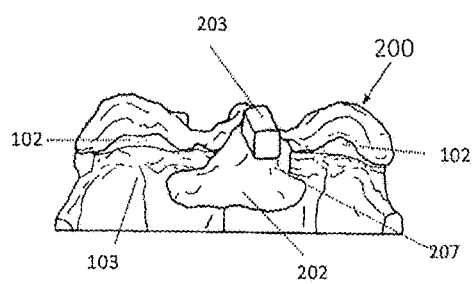
FIG. 2B is a side view of the exemplary base frame for the upper jaw on FIG. 2A diagnostic model.
Figure 2C:
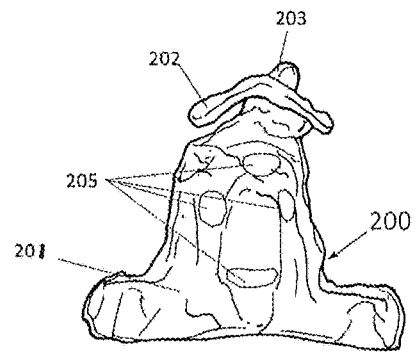
FIG. 2C is a bottom view of the exemplary base frame for the upper jaw shown in FIG. 2A.
Figure 2D:
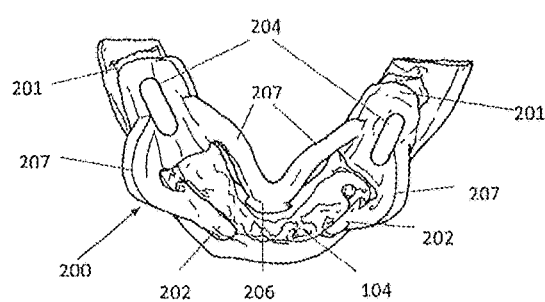
FIG. 2D is a top view of an exemplary base frame for a lower jaw on a diagnostic anatomical model with gum tissue and a partially exposed bone structure.
Figure 2E:
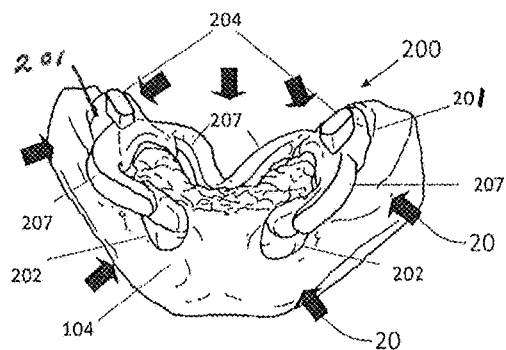
FIG. 2E is a perspective front view of the exemplary base frame for the lower jaw on the same anatomical diagnostic model shown in FIG. 2D.

FIGS. 2A-E are exemplary designs of a base frame 200 for an upper jaw (FIGS. 2A-2C) and a lower jaw (FIGS. 2D & 2E). The base frame 200 may be made of a transparent or semi-transparent resin or other composite material that gives the surgeon maximum visibility of the surgical site, but it may also be made of a colored resin and other composite material or metal that provides the base frame 200 with enough rigidity for stability and the right amount of flexibility in clasping areas. In order to obtain rigidity and flexibility in different areas, the frame 200 may be designed to have thick areas and thin areas accordingly within the frame. Overall however, the base frame can be more flexible than one piece surgical guide since the surgical drill guide section placed on top of it can solidify the whole drill guide assembly and the flexibility allows the device to clasp on to the undercut easily. The base frame 200 is shown positioned on top of the upper jawbone structure 103. A plurality of osteotomies of simulated dental implant placements 105 are shown about the periphery of the upper jawbone structure 103. A handle 203 is secured towards a forward portion of the base frame 200 which is used to aid in the maneuverability of the base frame 200. Interlocking connectors 204 are firmly mounted to, or formed part thereof, the base frame 200, and provide guides for the surgical drill guide housing frame 300 to connect thereto. The arrows 20 depict potential pressure impinging points for the drill guide housing frame 300 to impinge upon.

FIG. 2D shows a base frame 200 on the type of anatomical models explained above, and gum tissue contact portions 201 are placed on the gum tissue areas of the model. Although this portion may have broad area contacts with the gum tissue 102, it may also have strategically placed smaller spot contact areas 205 as shown in FIG. 2C. In some designs, certain areas of gum tissue contact portion can be used to place temporary anchors through the gum tissue into the patient jawbone by small screws, pins or other fastening devices.

The surgical device 200 may also have one or more clasping lateral contacts 202 (See FIGS. 2B-2E) that may simply contact the lateral wall of the exposed jawbone 103 and 104 or engage its undercut. As shown in one exemplary design of the base plate 200 for a lower jaw 104 (FIGS. 2D & 2E), clasping lateral contacts 202 may be connected to the gum tissue contact portion 201 by stabilizing/clasping arms 207 that may or may not have contact with the oral structure. The stabilizing/clasping arms 207 extend out from a base frame 200 and/or drill guide housing frame 300 which may be turn into a drill guide housing section 400 with drill guide bushings. When the frame is placed on the oral structure or anatomical diagnostic model, the stabilizing/clasping arms 207 slightly flex out and then clasp securely onto the oral structure 104. Although the stabilizing/clasping arms 207 are illustrated as peninsulas that extend out of the tissue contact area, the stabilizing/clasping arms 207 may be continuously connected to the tissue area like in the exemplary base frame 200 shown in FIG. 2F. Clasping lateral contact area 202 may also be used for placing a temporary anchor directly into the jawbone 104 if the patient's oral structure does not allow the device to have enough retention.

Figure 12:
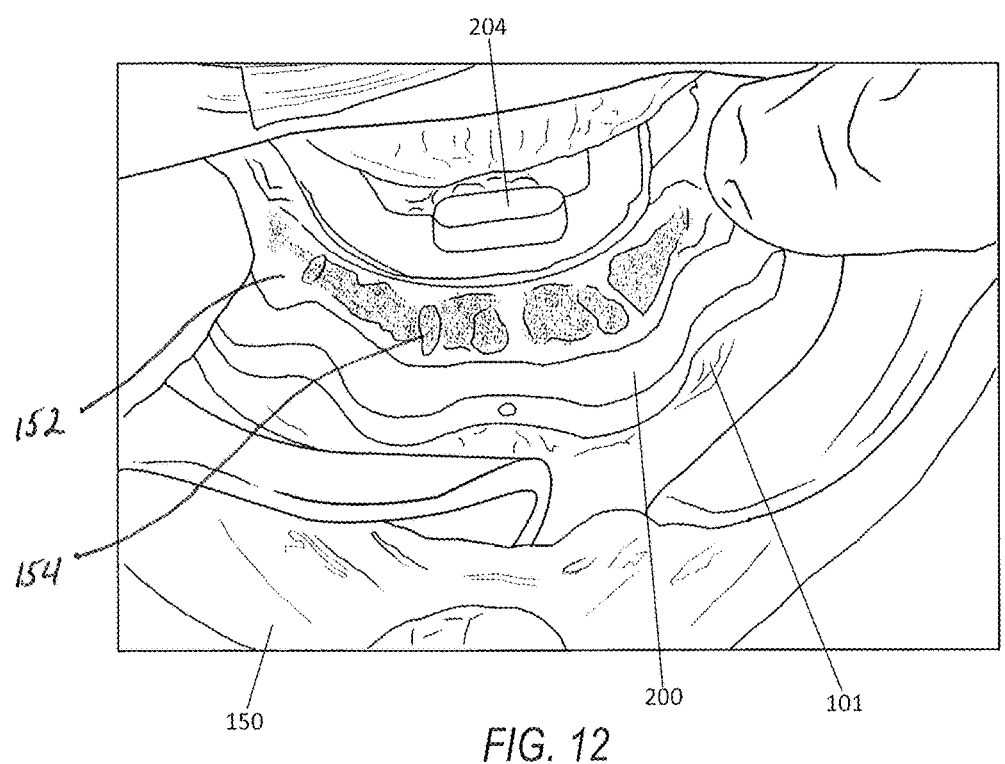
FIG. 12 is the base frame of the FIG. 9 drill guide assembly shown positioned within the mouth of a patient.

Similar to the clasping lateral contacts 202, one or more occlusal/lateral stabilizing rests 206 (FIG. 2D) may be strategically placed to contact the jawbone 104 to work along with the gum tissue contact portion 201 and the clasping lateral contact 202 in order for the device 202 to be securely positioned inside of the patient's oral structure (See FIG. 12). This section may also be connected to the gum tissue contact portion 201 by at least one stabilizing/clasping arm 207.

Figure 6A:
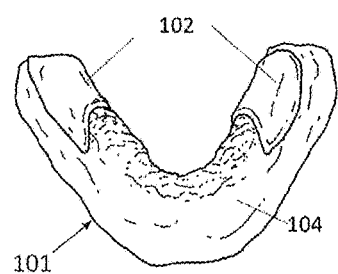
FIG. 6A is a perspective front view of an exemplary anatomical diagnostic model with a partially exposed lower jaw bone before adjustment.
Figure 6B:
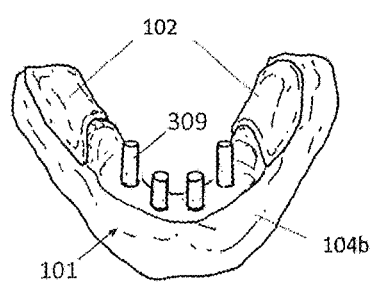
FIG. 6B is a perspective front view of the exemplary anatomical diagnostic model with a partially exposed modified lower jaw bone with planned osteotomies.
Figure 6C:
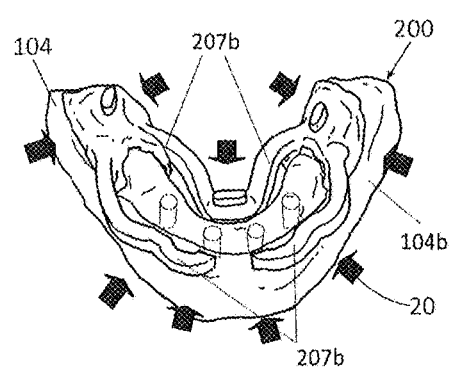
FIG. 6C is a perspective front view of an exemplary base frame on the diagnostic anatomical model.

The arrows on FIGS. 2A, 2E and 6C indicate the direction of force 20 applied from each contact point to the oral structure, and show how stabilizing/clasping arms 207 help fixate the device 200 in place.

Although it is not illustrated, due to a particular shape of the jawbone 103, 104, the base frame 200 may be designed to have only tissue contacts without any jawbone contact and to have a separate detachably attachable part that snaps onto it and engage the jawbone. Alternatively, this bone clasping part can be a latch connected to the base frame 200 by a hinge.

Figure 2F:
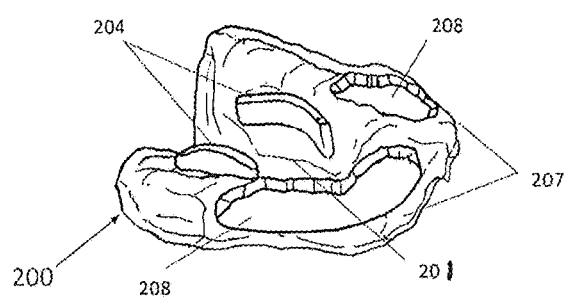
FIG. 2F is a perspective view of an exemplary base frame for the upper jaw.

The base frame 200 may also include a handle 203 on FIGS. 2A-2C that may be used when removing the device from the oral structure, and an interlocking connector 204 (FIG. 2A, 2B, 2D, 2E) that securely connects the base frame 200 to a surgical drill guide housing frame 300 (FIGS. 3A-3E, and FIGS. 4A, & 4C). The handle 203 may also be a handle/connector, a part of which works as a male interlocking connector. FIG. 2F illustrates the base frame 200 having connectors 204 that are secured to the upper service thereof. Stabilizing arms 207 are positioned around its outer periphery with openings 208 being positioned adjacent thereto.

FIG. 3A illustrates an exemplary drill guide housing frame 300 configured to be disposed on the base frame 200, which collectively form an assembly 310. Material requirements for the drill guide housing frame 300 are same as the specifications for the base frame 200. The drill guide housing frame 300 may securely snap onto the base frame 200 by the interlocking connectors 204 (FIGS. 2A, 2C, 2D, 2E) and the connector receptors 304 (FIG. 3B), also by the handle 203 and handle/connector receptors 303 (FIGS. 3A-3D), along with various stabilizing rests and/or clasping contact areas between the two devices 200, 300. As illustrated, the interlocking connectors 204 on the base frame 200 may be male connectors with strategically placed slight undercuts, and the connector receptors 302 and 303 on the drill guide housing frame 300 may be female connectors. However, various types of different connector mechanisms can be used for this purpose. Similar to the handle/connector 203 on the base frame 200, the handle/connector receptor 303 may be used when removing the device from the base frame 200, and it may also be used as a receptor for the handle/connector 203. Similar to the contact points/areas of the base frame to the oral structure, the drill guide housing frame 300 may have clasping or resting contact points/areas to the base frame 200 besides the connectors. These contact points/areas may be strategically placed to work together along with the connectors not only to ensure a secure fit of the part to the base frame 200 but also to lock in the entire device (the base frame and the drill guide housing section) onto the oral structure by adding an extra layer of thickness and applying more clasping force. The base frame 200 and the surgical drill guide housing 300 may be designed to work together to make the assembly 310 set snugly fit onto the oral structure 100 and yet have great rigidity so that it is very stable in the patient's mouth as well as on the physical anatomical diagnostic model. Although not illustrated, the frames may be fastened together using any other suitable fasteners including, but not limited to, screws, pins and latches.

Figure 4A:
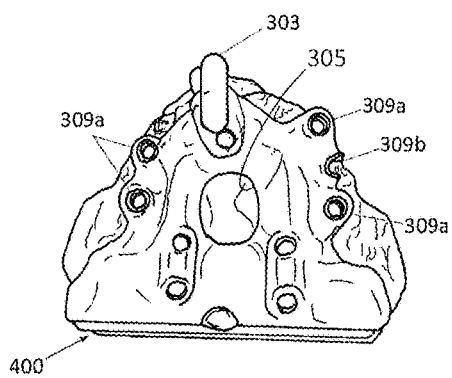
FIG. 4A is a top view of an exemplary drill guide section for the upper jaw placed on the base frame and the physical anatomical diagnostic model.
Figure 4B:
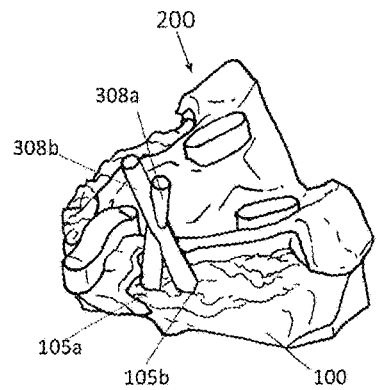
FIG. 4B is a perspective view of the FIG. 4A anatomical diagnostic model with base frame and positioning pins, showing intersecting osteotomy angulations.
Figure 4C:
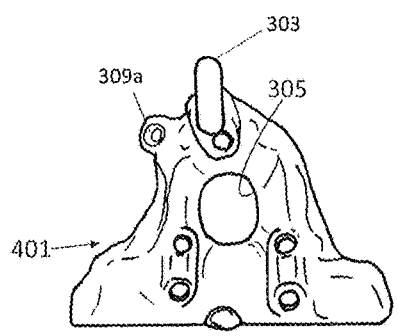
FIG. 4C is a top view of an exemplary interchangeable additional drill guide section with a tube surgical drill guide bushing.

The holes 304 on the connector receptors 302 and handle/connector receptor 303 shown on FIGS. 3B and 3D are liquid escape holes 304 that allow excess moisture and debris to escape so that they will not be trapped in-between the devices 200 and 300. It should be noted that the liquid escape holes 304 can be created in different areas of the drill guide housing frame 300. The larger opening holes 305 in the middle of the devices 300 and 401 in FIGS. 4A and 4C are clearance openings for fastening anchor devises such as screws and pins that are used to fasten the base frame 200 onto the jawbones 103 and 104 without engaging with the drill guide housing frame 300. However, the larger opening holes 305 may also be used as liquid escape holes 304.

Unlike the handles 203 and 303, other exemplary handles may not have a connecting function. The handles may be on either one or both of the base frame 200 and the drill guide housing frame 300, and there may be more than one handle 203 and 303 on both frames. Moreover, the handles on the base frame 200 and the drill guide housing frame 300 can work together as a combination handle unit. Ideally, the combination handle unit is designed to leave a small space at least in a certain area between the devices' handles so that a hand instrument or other types of tools can be inserted into the space to pry the frames apart. Also, similar spaces 601 for the instrument may be created between the frames in other areas to make the separation of the frame easier. See FIGS. 6D, 8 and 11.

Optionally, the device may also feature skirted areas 301 (FIG. 3B) over the intended surgical site(s). This feature may be useful when the surgeon plans the osteotomies 105 on a physical anatomical model and the device is rapid prototyped or CNC milled from the design created on the digital anatomical model. The skirted areas may be a thin shell that extends from the device 300 and covers the intended surgical site(s). The purpose of this feature is to provide base structure for the surgical drill guide site(s). When the osteotomies are planned on a rapid-prototyped or milled physical anatomical model, the implant positions and angulations are unknown at the time of manufacturing of the surgical drill guide frame or frame set. By having a thin skirted area 301 over the intended implant site as a base structure, it may be easier to prepare the surgical drill guide site(s) on the device 300. Also, the skirted area 301 can be made so that the top surface or the bottom surface of the section represents the patient's gum tissue 102. It can also be made so that the bottom surface of the section sits on top of the bone, a certain distance away from the bone below or above the gum tissue. By going through the procedure that is shown on FIG. 3C, the holes 306 that correspond with the planned osteotomies 308 will be created on the skirt as shown on FIG. 3D. Drill 306 is used to create the holes 306. When the surgical drill guide sites are prepared on the physical anatomical model 100, positioning pins 308 may be used to set the angulations of the osteotomies and to position the surgical drill guide parts 309 as shown in FIG. 3E.

Figure 4D:
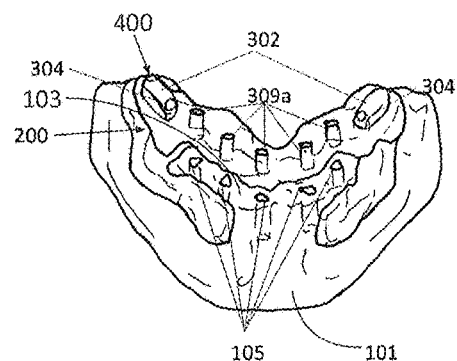
FIG. 4D is a top view of an exemplary surgical drill guide section for the lower jaw placed on the base frame and the physical diagnostic anatomical model.

FIG. 4A illustrates an exemplary surgical drill guide section 400 that was trimmed after surgical drill guide sites are prepared so that the device 400 may provide improved surgical site visibility and good facility for irrigation. Optionally, metal or ceramic tube type 309a or open-face type 309b surgical drill guide bushings can be attached to the device 400, but the device may not have any added parts to the drill guide site. If the implant placement is digitally planned on the digital anatomical model prior to the model manufacturing, the drill guide housing frame 300 can be digitally designed like this illustration, without any skirted area 301, so that the drill guide bushings 309a and 309b can be attached to the device 400 right after manufacturing. Another exemplary surgical drill guide section 400 shown in FIG. 4D for a lower jawbone 101 snapped on to the base frame 200 illustrates the space 105 between jawbone surface 103 and the bottom of the drill guide housing frame 400 over the surgical site, which may be preferred by surgeons for the better irrigation. However, as previously described, the bottom surface of the drill guide housing frame may be set at a different height.

Figure 5:
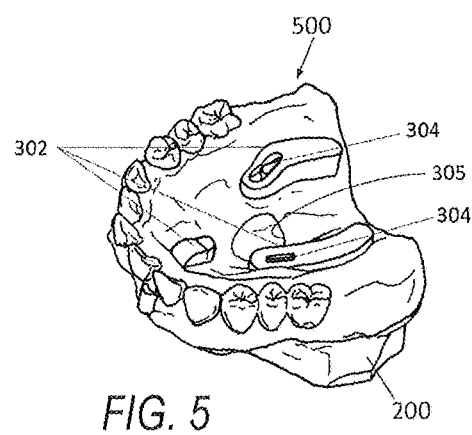
FIG. 5 is a perspective view of an exemplary modified denture duplicate attachment for an upper jaw attached to a base frame.

FIG. 5 illustrates the modified duplicated denture appliance 500 attached to the base frame 200. One way of creating this appliance is to scan the patient's denture or duplicated denture surfaces, align the data to the anatomical model, and modify it to fit on the base frame 200. This appliance 500 may have features such as connector receptors 302, irrigation holes 304, and openings for fastening anchor devices 304 just like a surgical drill guide housing frame 300. This appliance 500 may be used to verify the position of the base frame or the single piece surgical guide with patient's bite. Other examples of attachments include, but are not limited to, an implant pick up impression tray, an implant transfer jig tray, and a bone adjustment jig.

Advantages of the drill guide assembly 310 having the base frame 200 and the drill guide housing frame 300 may include: 1) Interchangeable multiple guide frames 300 can be used during the surgery while the base frame 200 can be securely positioned in the patient oral structure; 2) If, for any reason, the doctor changes the positioning of one or more of the implants from the original plan, and cannot use the surgical drill guide for those particular site(s), or needs to work on the bone, he/she can temporarily remove the drill guide housing frame 300 from the base frame 200 without disturbing the position of the base frame 200; 3) Various types of additional attachments can be placed on the base plate 200 without the drill guide parts covering the surgical sites. The drill guide assembly 310 is especially beneficial when the base frame needs to be temporarily anchored to the patient's jawbone.

More than one surgical drill guide section 400 may be needed in order to accommodate a surgery's specific needs. As illustrated with the positioning pins 308a and 308b in FIG. 4B, two of the intended osteotomies 105a and 105b are very close to each other and have intersecting positioning angulations. In this case, a second surgical drill guide section, 401 in FIG. 4C may be created for one of the planned osteotomies 105a. This type of additional surgical guide section 401 is detachably attachable to the base frame 200 and is interchangeable with the first surgical drill guide section 400. Alternatively, smaller parts that house the surgical drill guide bushings 309 or drill guide holes for specific implant placement sites may be attached to the first surgical drill guide section 400. Although it is not illustrated, another benefit for having additional surgical drill guide section 401 is to accommodate larger size surgical drill guide bushings, 309a and 309b that are subsequently used for finish drilling osteotomies 105.

FIGS. 6A-6D represent a situation in which the doctor decides to reduce the jawbone prior to implant placement. FIG. 6A is an anatomical diagnostic model of a lower jaw 101 which shows a gum tissue portion 102 and a partially exposed bone structure 104. The doctor may wish to modify the bone 104b prior to the implant placement as in FIG. 6B. In this case, the base frame 200 (FIG. 6C) may be designed according to the doctor's specification either on the digital model or the physical anatomical diagnostic model so that it can be used as a bone reduction jig. FIG. 6C illustrates a base frame (200) on an anatomical diagnostic model with a modified lower jawbone 104. A drill guide section 400 FIG. 6D may be designed on top of the base frame 200 to be used for implant placement.

Various types of additional detachably attachable appliances can be added to the surgical drill guide 400. One example of an additional appliance is a modified duplicated denture attachment 500.

Figure 7:
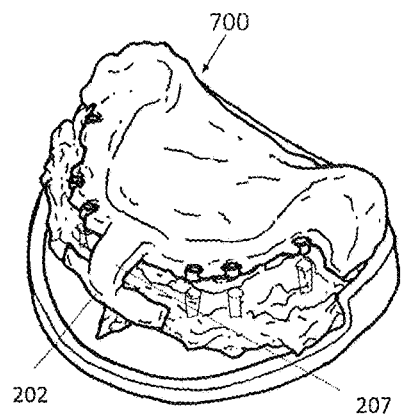
FIG. 7 is a perspective view of an exemplary one piece drill guide on a physical anatomical diagnostic model.

It will be appreciated that the surgical drill guide can be manufactured as single piece 700 (FIG. 7) that contacts both gum tissue and exposed bone. Single piece apparatus 700 has combined functions of both base frame 200 and the surgical drill guide section 300. The device may have all or some of the features described above, or it may include different types of attachments. Lateral contacts 202 on the forward edge are connected to an arm 207, which may be a part of the single piece guide 700.

Figure 6D:
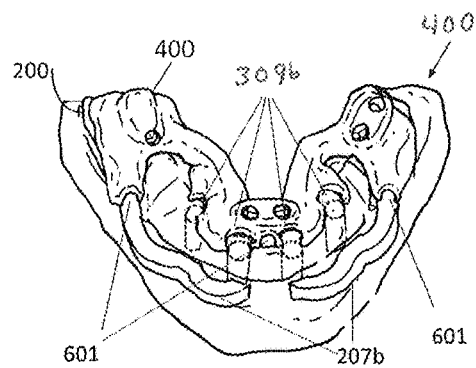
FIG. 6D is a perspective front view of an exemplary drill guide section placed on the base frame and the anatomical diagnostic model.
Figure 8:
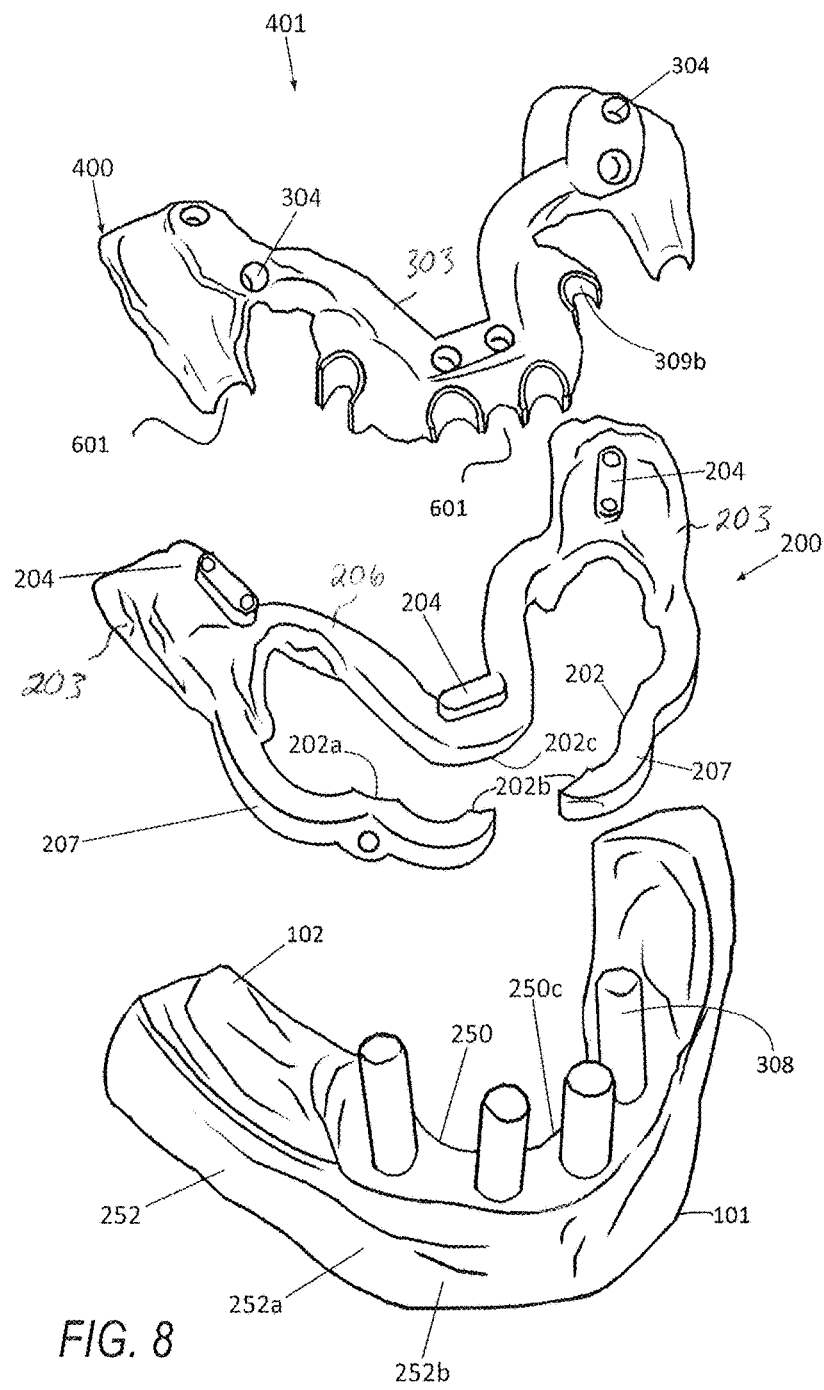
FIG. 8 is an exploded perspective view of the FIG. 6D drill guide assembly.

FIG. 8 is an exploded view of a two part surgical drill guide assembly 401 that is shown in FIG. 6D. The assembly consists of the surgical drill guide section 400 and the interlocking base 200. Collectively, the drill guide section 400 and base 200 can be snapped together and strategically placed relative to the lower jaw 101 which, in this instance, is a physical diagnostic anatomical model of a lower jaw for a human being. The base 200 has a base member 203 at a rearward portion, a first outwardly extending clasping or stabilizing arm 207, and a second arm 206 that extends from the base member 203. The arms have flattened portions and are resilient for placing a force on a jaw. The base 200 is operable to be received on the lower jaw 101 and located relative to the interior 250 and exterior 252 surfaces of the lower jaw 101. In particular, the base 200 further has lateral contacts 202 at internal locations, which are strategically located to impinge upon exterior surface 252 of the lower jaw 101. For example, lateral contact 202a is operable to impinge upon exterior contact 252a. Likewise, lateral contact 202b is designed to strategically impinge upon contact surface 252b in two locations relative to the exterior surface 252 of the lower jaw 101. Likewise, lateral contact 202c is located on an outwardly extending portion of the base frame 200, and is operable to engage interior surface 250c of the lower jaw 101. These contact points, and others, are designed to impinge forces 20 (See FIGS. 2A, 2E and 6C) for aiding and positioning, the base frame 200 relative to the lower jaw 101.

Once the base frame 200 has been positioned relative to the lower jaw 101, the surgical drill guide section of 400 has receptacles that are snapped to interlocking connectors 204 that, in the exemplary model, are positioned at three locations about the base frame 200. It will be appreciated that more, or fewer, interlocking connectors 204 can be provided. The locking fit between the interlocking connectors 204 and the corresponding female receptacles that are on the underneath side of the surgical drill guide section 400, create a snap-fit type connection. This snap-fit configuration provides for ease of separability of the drill guide section 400 and the base frame 200, as well as provides a self-centering locating arrangement for making sure the assembly 401 is properly fit together. The drill guide section 400 includes a flattened center potion 303 that has a plurality of bushings 309a or 309b extending through the flattened portion. The drill guide section 400 further may have water escape holes 304, along with the open face drill guide bushings 309b, as well as a separation feature or openings 601 at three locations, which aid in separating the drill guide section 400 and the base frame 200. The openings 601 are sufficient to allow a device, for example a dental instrument, to be inserted between the drill guide section 400 and the base frame 200, so as to allow ease of separation of the two components.

The open face drill guide bushings 309b provide a guide mechanism for receiving positioning pins 308. The bushings are preferably made of metal and they are anchored in the guide section 400. The positioning pins 308 may be made of metal or hard plastic and are placed into the planned osteotomies within the lower jaw anatomical diagnostic model 101 and are configured to receive the bushings 309b, which helps align the drill guide 400 relative to the jaw 101. At the surgery, drill guide bushings guide the drills to create osteotomies for implant placement.

Figure 9:
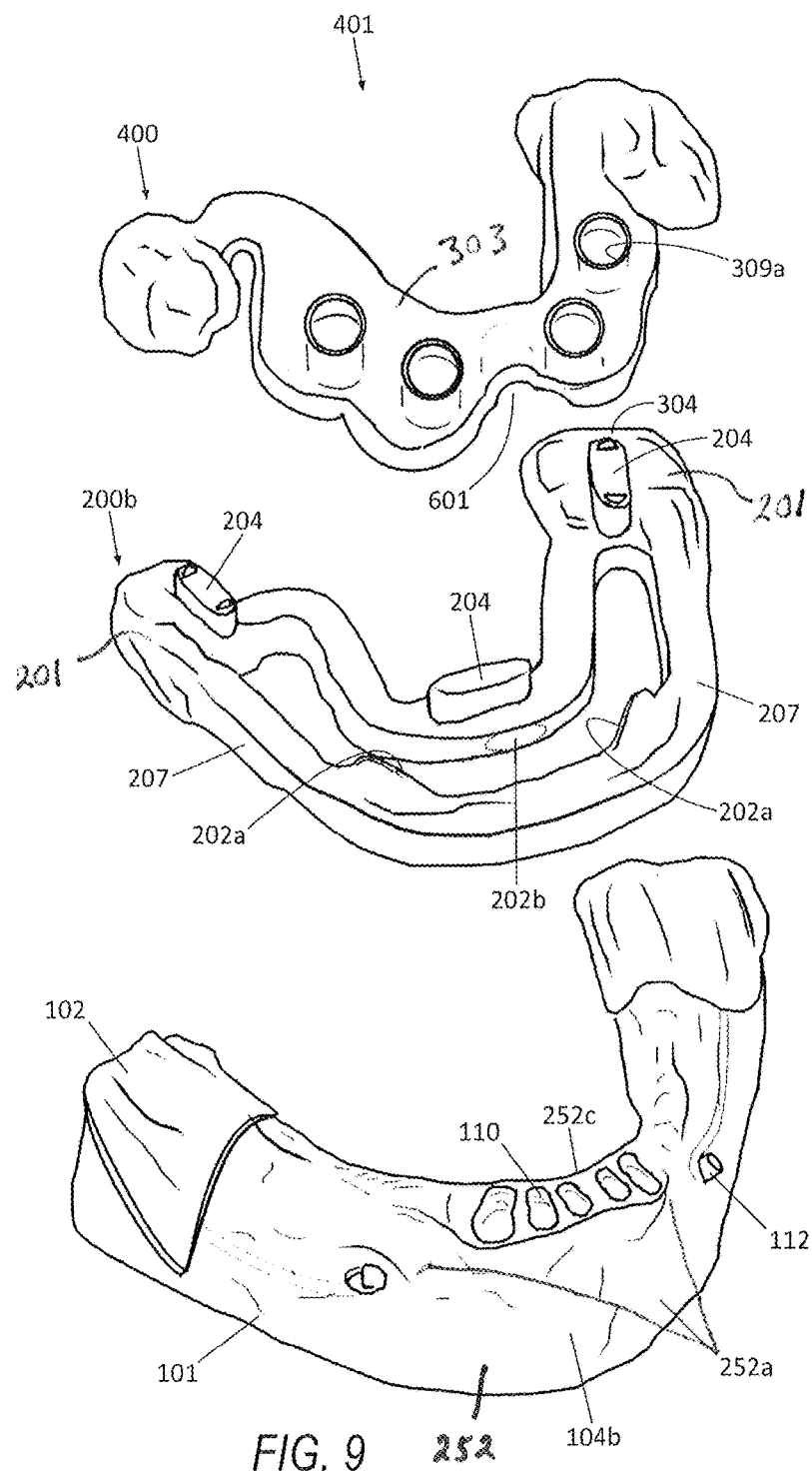
FIG. 9 is an exploded perspective view of another exemplary drill guide assembly.

FIG. 9 illustrates another exemplary drill guide assembly 401 including a drill guide section 400 and a base frame 204b, which also works as a bone reduction jig. The assembly 401 can be positioned relative to exposed bone area 104b of a lower jaw 101, which, in this visual, is a diagnostic anatomical lower jaw model. This particular lower jaw model 101 includes extracted teeth sockets 110, which can be either recently extracted teeth or digitally simulated planned teeth extraction, a gum tissue area 102, and nerve endings 112. The base frame 200b has interlocking connectors 204 formed on the upper surface of the base frame 200b that can be integrally molded to the base frame 200b. Lateral contacts 202a and 202b are positioned about an interior surface of the clasping arm 207 and form pressure points for impinging upon exterior surface 252 of the lower jaw 101 at points 252a, and 252c, respectively.

The surgical drill guide section 400 is shown ready to be positioned and connected to the base frame 200b. Drill guide bushings 309a are provided within holes for receiving positioning pins 308. An opening 601 is provided to help in separating the drill guide section 400 from the base frame 200b.

Figure 10:
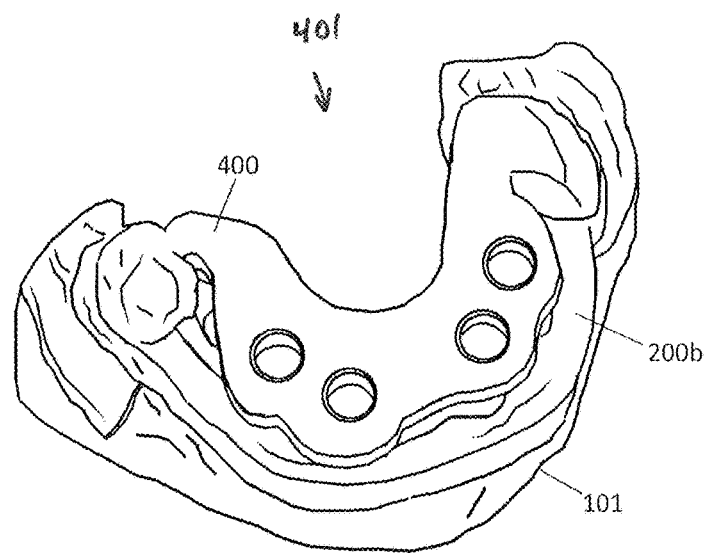
FIG. 10 is the FIG. 9 drill guide assembly in assembled form.

FIG. 10 illustrates the FIG. 9 surgical drill guide assembly 401 in an assembled condition. The drill guide 400 is shown in place relative to the base frame 200b which in turn, is positioned relative to the lower jaw 101.

Figure 11:
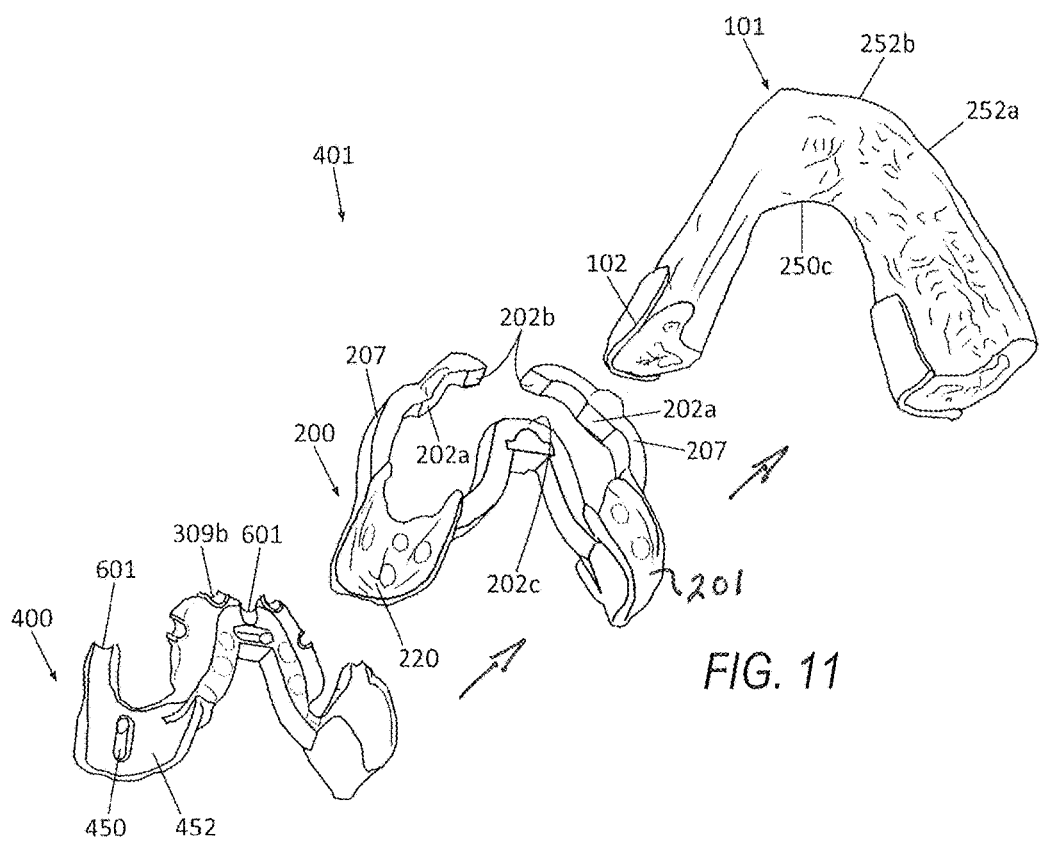
FIG. 11 is a bottom perspective exploded view of the FIG. 8 assembly.

FIG. 11 illustrates a bottom perspective view of the FIG. 6 surgical drill guide assembly 401. From this perspective, the underside of the base frame 200 and the drill guide section 400 can be more readily observed. The lower jaw 101 is shown with gum tissue 102. The Base frame 200 has scalloped or saddle shaped tissue contact portions 220 that are received by the gum tissue areas 102 of the lower jaw 101. The clasping arm 207 has impinging areas 202a and 202b that impinge upon surfaces 252a and 252b, respectively, of the jaw 101. Likewise, impinging surface 202c impinges upon corresponding internal surface 250c of the jaw 101 so as to provide an inwardly impinging force 20 as previously depicted in FIG. 6C.

The surgical drill guide section 400 has receptacles on the underside surface 452 that are operable to lockingly engage with interlocking connectors 204 (FIG. 9) of the base frame 200. Openings 601 provide a gap between the surgical drill guide 400 and the base frame 200 so as to allow for ease of separation between these two components. The recess 450 is slightly larger in physical configuration than the interlocking connector 204. The interlocking connector 204 is sufficiently resilient, as is the receptacle 450, so as to provide a positive snap-fit locking configuration between the components 400 and 200. Once together, an interlocked assembly 401 is created, which can be easily aligned relative to the jaw 101.

FIG. 12 illustrates a perspective view of the base frame200, which is functioning here as a bone reduction jig, being positioned relative to the lower jaw 101 in the context of a mouth 150. It depicts the lower jawbone having a shaved section 152 according to the clasping arm portion of the base frame 200. Extracted teeth sockets 154 are present and depict the location of the extracted teeth. An interlocking connector 204 is shown and is operable and ready to receive the surgical drill guide section 400 (not shown).

Figure 13:
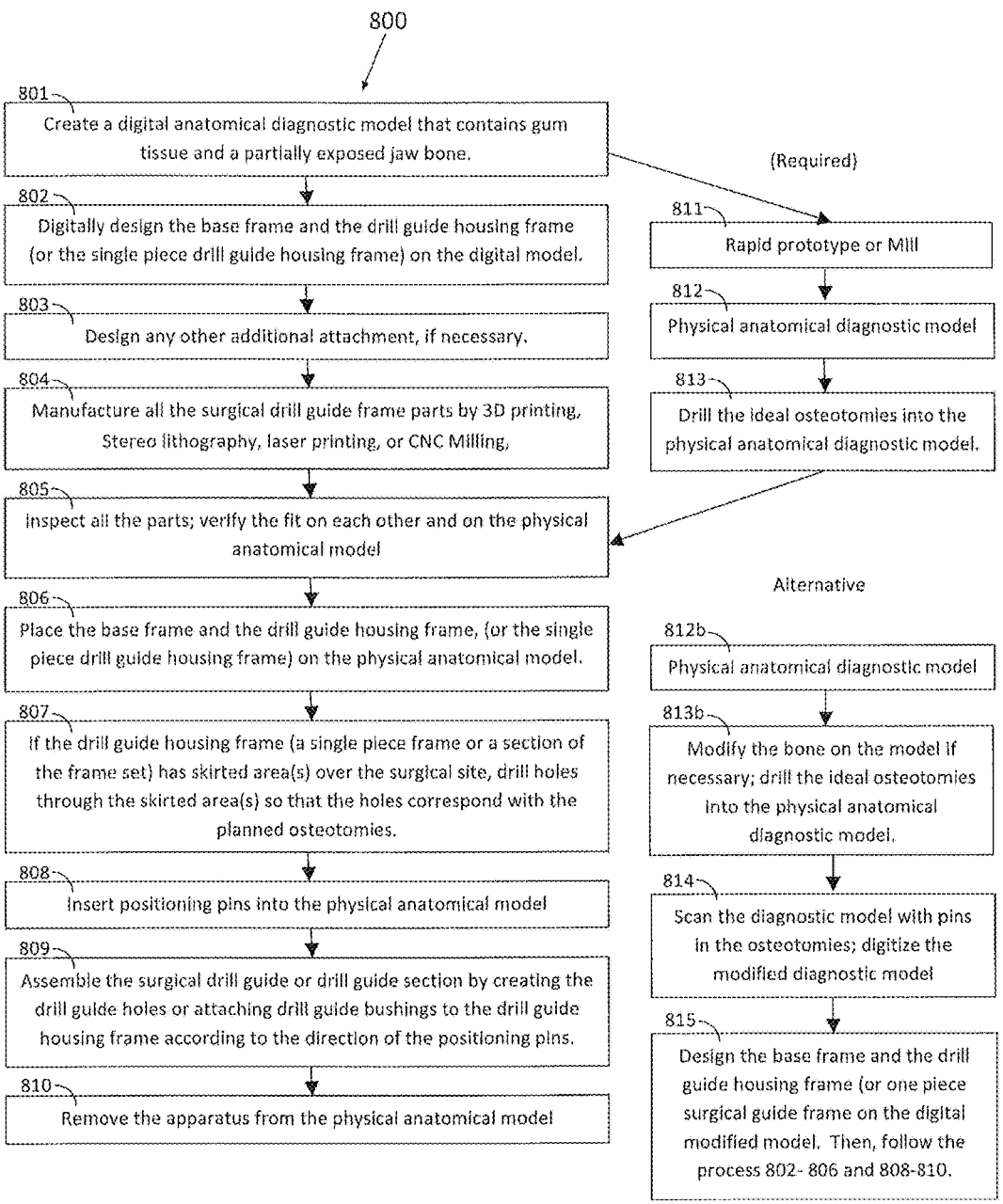
FIG. 13 is a diagram of the edentulous surgical drill guide manufacturing process for a model based implant placement planning.
Figure 14:
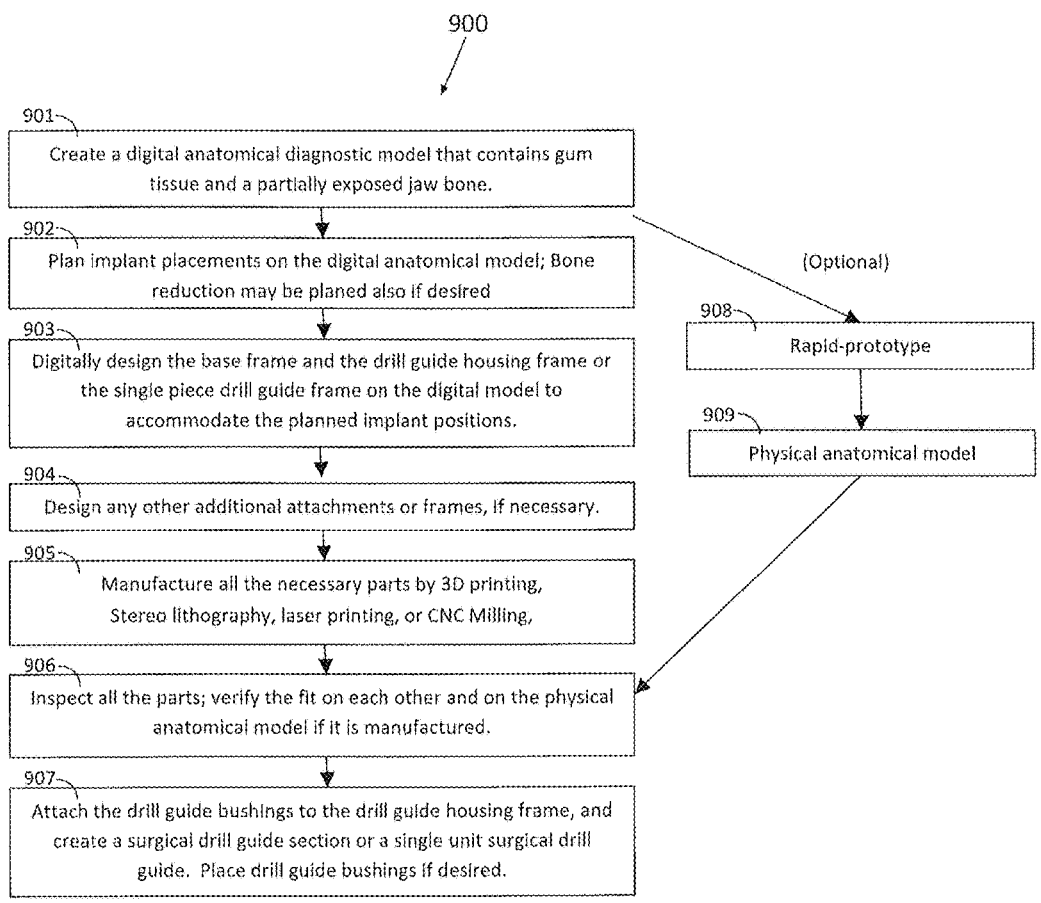
FIG. 14 is a diagram of the edentulous surgical drill guide manufacturing process for a digital implant placement planning.

FIG. 13 and FIG. 14 show different manufacturing methods of using an edentulous surgical drill guide or assembly 401. FIG. 13 illustrates a model based implant placement planning method 800 and FIG. 9 illustrates a digital implant placement planning method 900. Both methods start with a digital anatomical diagnostic model, with partially exposed jawbone 101 in the area of interest, in a file format such as STL that allows reverse engineering and 3D modeling 801 and 901. The digital anatomical diagnostic model 801 can be obtained by accurately aligning the surface scan data of the patient's mouth or dental cast and the tomography scan data that is volume rendered and converted to a compatible file format. Since all the devices are patient specific, the design and features of the apparatus is planned according to the patient's oral structure, bone condition, and the surgical needs. Although the apparatus can be created as one single surgical guide as described in the diagram in FIG. 7, the same or similar procedure may be applied when using a multiple piece guide.

In both methods, a technician digitally designs the base frame 200, and the drill guide housing frame 300, along with additional frames and attachments, if any, using reverse engineering software program such as Geomagic, Radidform, and 3 Matics, optionally combined with 3D modeling software such as Rhinoceros 3D and Solidworks (See steps 802, 902, 803 and 903). The base frame 200 (FIG. 2) can be designed first on the digital model with partially exposed bone just in the area of the surgical site 802 and 902 and then the drill guide housing frame section 300 (FIG. 3) can be designed on both the digital anatomical diagnostic model and the base frame (802 and 902). By doing so, the surgical guide can be designed to obtain better fit and stability, because 1) it avoids bone contact in the areas where the density of the bone is too close to that of the soft tissue for its contour to be accurately defined in the CT images when the bone is porous, and 2) it also clasps onto rigid bone areas instead of contacting the malleable tissue surface alone. Subsequently, if additional frames or attachments are needed, they can be designed to fit on the base frame 200 and/or the surgical drill guide housing frame 300 according to the part's function 803 and 903. Some of the features and functions of the apparatus are the same or similar for the model based implant placement planning or the digital implant placement planning. However, several differences may be found in features and methods between for these two situations.

FIG. 13 illustrates a workflow 800 of a model based surgical planning. When the implant placement is planned on an aligned physical anatomical diagnostic model 812 created by rapid prototyping 811 the digital model 801, the technician needs to design the drill guide housing frame or housing frame section 300 on the digital anatomical diagnostic model without knowing the exact plan of implants' positioning. Naturally, the device is designed as a base structure of the surgical guide that will be assembled manually on the physical anatomical model. Thus, the device often has the skirted area 301 (FIG. 3B) that extends over the intended site so that it is easier for the clinician or technician to assemble the surgical drill guide later on a physical anatomical diagnostic model (See steps 806-809). Similarly, other special parts that work on the physical model may also be designed to aid the surgical guide assembly. Meanwhile, a physical anatomical diagnostic model is manufactured by rapid prototyping or CNC milling (See steps 811-812), and ideal osteotomies are simulated on the physical anatomical diagnostic model by a qualified clinician (Step 813). Alternatively, the modified anatomical diagnostic model with positioning pins placed into the osteotomies can be digitized by surface scanning (Step 814), and the drill guide 200, 400 or 700 may be designed on the modified digital anatomical diagnostic model. If bone reduction is planned on a physical anatomical diagnostic model then the doctor can drill the ideal osteotomies into the physical model, (See step 813b).

After all the parts are designed on the digital diagnostic model, they are manufactured by rapid prototyping such as 3D printing and stereolithography or CNC milling 804, cleaned, inspected, and verified on the physical anatomical model 805. Place the base frame and the drill guide housing frame 200 on the physical anatomical model 100, as shown in step 806.

If the drill guide housing frame has skirted areas 301 (FIG. 3B) over the surgical site, drill holes may be placed through the skirted areas 301 with a hand piece 306 (FIG. 3C) so that the holes correspond with the planned osteotomies. Since the drill guide housing frame is usually made with a transparent or semi-transparent material, the simulated osteotomies on the model is visible thorough the thin skirted areas 301, and corresponding holes can be made. Positioning pins 308 may be inserted into the osteotomies on the anatomical model through the holes of the skirted areas 808. Drill guide bushings 309 may be placed with respect to the positioning pins 308 and the bushings' distance may be set from the oral structure according to the preference. As briefly described above, the top or the bottom of the skirted areas 301 may be set at, below or above the gum tissue surface 102.

Alternatively, the bottom of the skirted areas 301 may be made to contact the exposed bone. If the diameter of holes on the skirt is close to the inner diameter of the drill guide bushing, the bushing can rest on the skirted areas. The holes of the skirted areas 301 may also be made larger so that extra parts to control the height can be inserted onto the positioning pins 305. It should also be noted that the drill guide housing frame 300 may be configured to accommodate various types of interchangeable drill guide bushings as well as most of depth control surgical guide system parts sold by various implant companies. After the positions are set, the bushings maybe attached to the drill guide housing frame with light cured composite or other adhesive materials 809. Additional light cured composite may be added to the frame to increase the rigidity of the device. Light cured composite may be added around the positioning pins on the skirted areas 301 instead of bushings to conform drill guide holes or slots. When finished, the positioning pins may be removed from the physical anatomical model 810. The skirted area can be then trimmed by a hand piece as previously described. Additional drill guide frames, if any, can be made by repeating the process. With a model based implant placement system, it may also be possible to manually create a surgical drill guide that clasps the gum tissue and the jawbone with similar features without any digitally designed frame structures. It should be noted that the skirted area may not be necessary if the anatomical diagnostic model is surface scanned after the doctor drills the osteotomies, and the apparatus is designed on the modified digital model.

FIG. 14 illustrates a flowchart of digital surgical planning. When the implant placement is planned digitally on an aligned digital anatomical diagnostic model 902 as illustrated in FIG. 14, the creation of physical anatomical diagnostic model may be optional. In this case, the technician can design the drill guide housing frame according to the simulated osteotomies on the digital anatomical model. Thus, there may be no need to create any skirted area. The support structure and receptor sites for the drill guide bushings can be digitally designed 903 so that the device is ready to receive the parts after prototyping. If any drill guide bushing parts with depth control function are going to be used, the device can be designed to receive those parts at the exact locations to accommodate the function. If the jaw bone 101 is reduced on the digital anatomical diagnostic model, the base frame 200 may be designed to function as a bone reduction jig.

Similar to the method for a model based implant placement system, the drill guide housing frame 300 is manufactured, along with the base frame and other additional frames and accessories, by rapid prototyping or CNC milling 905. After cleaning and inspection 906, the preferred drill guide bushings 309 can be placed into the drill guide frame 300 and secured by light cured composite or other adhesive material. For some type of drill guide bushings (309) adhesives may not be needed. The drill guide may also be created with built-in drill guide holes or slots without any separate parts if the device is made of an appropriate harder material such as metal.

Figure 15:
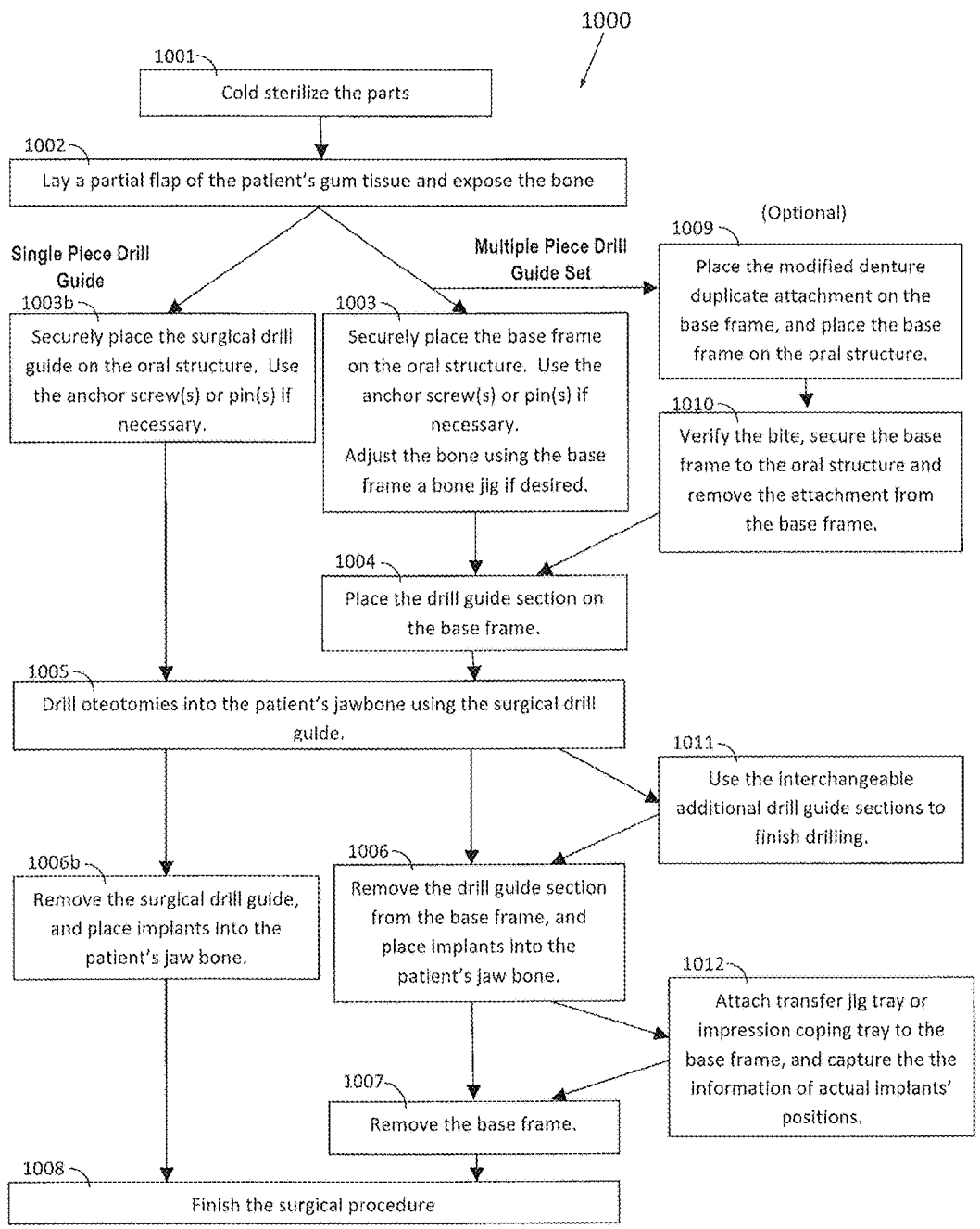
FIG. 15 is a diagram of how to utilize the edentulous surgical drill guide during the surgery.

FIG. 15 illustrates a flowchart of how the apparatus 401 can be utilized 1000 during an implant placement surgery. It will be appreciated that the steps can be modified, yet remain within the spirit of the exemplary illustrations herein. It should be noted that there are many variations to the workflow, and this chart is not intended to teach the surgical procedure itself. As is the case with the explanation of diagrams in FIG. 13 and FIG. 14, the following explanation is directed to a multiple piece drill guide system 401.

Prior to the surgery, all the parts of the drill guide set 401 are properly sanitized according to the material's requirement. For example, if the parts are rapid prototyped with resin, cold sterilization methods may be appropriate. However, heat sterilization may be used for different materials with high temperature tolerance 1001. Lay a partial flap of the patient's gum tissue to expose the jawbone in the area of interest 1002. In rare occasions, the surgeon may choose to flap only the areas that the bone clasping contact portions of the devise will contact with, leaving the gum tissue over the implant sites. The base frame 200 or the single piece surgical drill guide 300 may be securely placed on the oral structure 100 and in contact with both gum tissue and the exposed bone (See steps 1003 and 1003*b*). Additional attachments may be added to the device for bone clasping. Depending on the patient's oral structure, anchor screws or pins may be used for securing the position of the device. Bone adjustment or bone grafting may be done before or after the placement of the base frame 200. If the bone adjustment is needed, the base frame may be used as a jig or an additional bone adjustment jig can be attached to the base frame 200 for this process.

Optionally, a modified denture duplicate attachment 500 (FIG. 5) can be used on the base frame 200. In that case, verify the device's poisoning with bite to secure the base frame 200 to the oral structure, and then remove the attachment portion, leaving the base frame 300 on the oral structure 1009 and 1010.

After the base frame is securely placed, attach the drill guide section 300 to the base frame 200 (step 1004) in order to drill osteotomies into the jawbone (step 1005). The interchangeable additional drill guide sections may be used to complete the osteotomies 1011. When finished, the drill guide section 400 may be removed from the base frame (200), and the implants may be placed into the jawbone (see step 1006). Should a certain type of surgical guide tube system be adopted into the drill guide frame 300, the surgeon may place the implants through the drill guide tube bushings 1009 prior to the removal of the drill guide section 400.

The surgeon may choose to take a fixture level index for the record of implant positions at this point. In that case, he/she may be able to do so by altering the surgical guide section 400 into a transfer jig tray or by using a separate transfer jig tray that attaches to the base frame 200 (See step 1012). One advantage of utilizing the drill guide section 400 is that the actual positioning information can be easily transferred back to the physical anatomical model. The model can be adjusted, if necessary, and the prosthesis can be created on it without making a separate brand new After the base frame is removed 1007 the surgeon can complete the surgery by placing cover screws or healing caps, and suturing the gum tissue over the cover screw or around the healing caps. Alternatively, the immediate loading procedure may be followed, and the prosthesis that had been designed on the digital or the physical anatomical model can be placed 1008.

As FIGS. 16A and 16B-1 and 16B-2 illustrate different examples of superstructures of a multiple piece stackable surgical guide set 1101 that is similar to the surgical guide set 401 discussed above that can be used for taking a physical positional index of installed implant components. The multiple piece stackable surgical guide set 1101, examples of which are shown with respect to guide set 401 in FIGS. 8, 9 and 11, may be designed on the digital dental anatomical diagnostic model in the form of digital preoperative dental model 100 modeled from at least one of tomography scan of a patient's mouth, surface scan of the patient's mouth, digital topography data of the patient's mouth, or digital topography data of the patient's existing removable dental prosthesis using a CAD software program, and each section of the surgical guide set 401 can be manufactured by rapid prototyping. The preoperative dental model 100 may have one or more modifications digitally added to the original scan or combination of scans according to the type of planned surgery. The modifications may include but not be limited to partial exposure of the bone, digital dentition extraction, and digital bone adjustment. All of the preoperative dental models and sections of the surgical guide set 401 are digitally stored within the master data file properly oriented to each other with coordinates. Alternatively, the preoperative model 100 may be manufactured as a physical dental anatomical model by rapid prototyping and a surgical guide set may be manually created on the physical model. It should be noted that the surgical guide set 401 may be designed to fit on one or more types of the patient's oral structures such as jaw bone, gum tissue, and remaining dentition and it may also be designed to fit on any types of existing artificial prosthesis such as old implants, crowns and bridges.

Figure 16A:
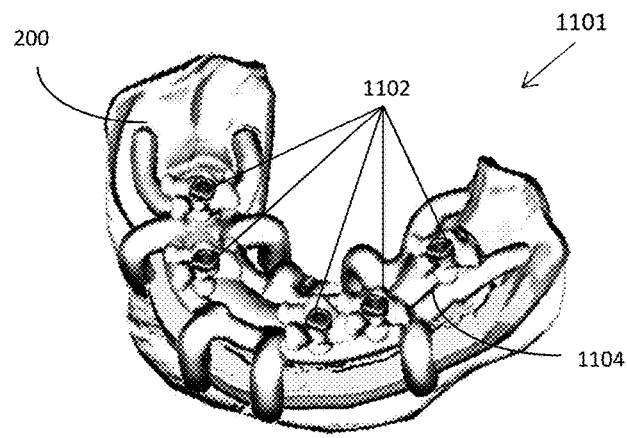
FIG. 16A is a perspective view of a transfer jig attached to an exemplary base frame of a multiple piece edentulous surgical guide set which is placed on the lower jaw of a patient.

FIG. 16A illustrates an exemplary transfer jig attachment 1104 acting as a transfer appliance, which is attached to the base frame 200 acting as a guide appliance and being used in a patient's mouth for taking a positional index of the installed implant components. The transfer jig attachment 1104 is a superstructure of the surgical guide set 1101 designed to receive at least one implant component 1102, such as an impression coping, scan body or temporary abutment, that engages and defines the fixed location of a corresponding installed implant in three dimensions. Engagement may include the implant and implant component 1102 being securely and repeatedly attachable to one another at a first end so that the components may be removed from a patient mouth and then re-engage the implant at a later date if necessary. A transfer appliance may have at least one opening over a planned implant site(s), which should be large enough to allow the top or opposing end of a corresponding implant component(s) 1102 to go through and to have some extra space around the transfer appliance so that it may engage an installed implant positioned at an implant site. This particular exemplary transfer jig attachment 1104 is designed for five corresponding implant components 1102, but a transfer jig attachment 1104 may be designed to receive any number of corresponding implant components 1102, and the connecting members and other parts of the design may differ from the exemplary transfer jig attachment 1104. The transfer jig attachment 1104 may be design to fit onto the base frame 200 or another foundation superstructure that is attachable to the base frame 200.

Figures 1, 16B:
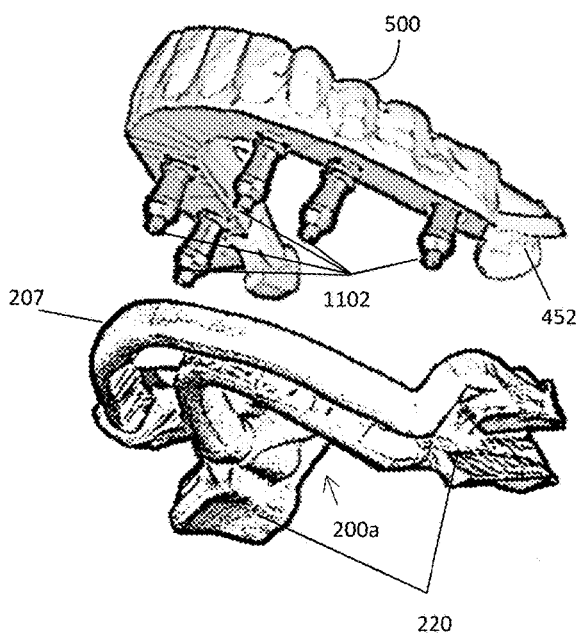
FIG. 16B-1 is an expanded bottom perspective view of an exemplary base frame and temporary prosthesis with connecting implant components.
Figures 2, 16B:
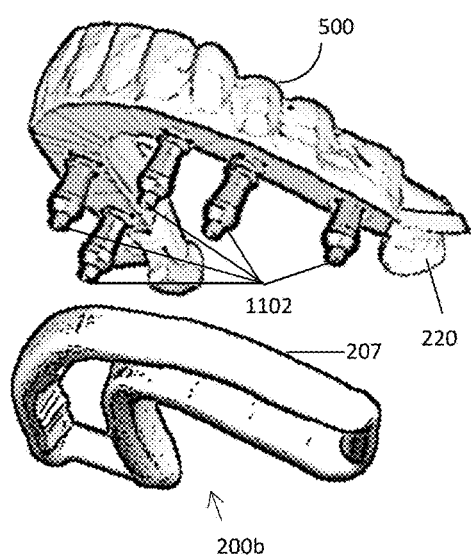

Alternatively, a temporary prosthesis, modified duplicated denture attachment 500 or other simulated diagnostic prosthesis can also be used as a transfer appliance. It should be noted that the same duplicated denture attachment 500 may also be used as a temporary prosthesis. FIGS. 16B-1 and 16B-2 are expanded bottom perspective views of exemplary assemblies of a base frame and modified denture/temporary prosthesis attachment combinations. Just like the transfer jig attachment 1104, the modified duplicated denture/temporary prosthesis attachment 500 may be designed to fit onto the base frame 200 or another foundation superstructure that is attachable to the base frame 200. FIG. 16B-1 illustrates the modified duplicated denture/temporary prosthesis attachment 500 that is indexed to the base frame 200a by at least one of the stabilizing/clasping arm(s) 207 of the base frame and underside surface 452. FIG. 16B-2 illustrates the same type of attachment 500 designed to fit onto the base frame 200b and also has contact portion 220 that directly contacts the patient's oral structure. Although the prosthesis in the form of attachment 500 can be an independent appliance designed on and indexed to the digital or physical preoperative dental model in order for it to be used as a temporary prosthesis and/or transfer appliance, if it is designed as a superstructure of the surgical guide set 401 as illustrated in FIGS. 16-B1 and 16B-2, it can be more easily positioned inside of the patient's mouth.

In order to use a transfer jig attachment 1104 or denture duplicate attachment 500 (either acting as a transfer appliance) associated with base frame 200 for taking a physical positional index of the installed implants, the procedure of FIG. 15 with a multiple piece surgical guide set should be generally followed. Using element 1104 as an example, after implants are installed (see e.g., elements 1303 representing implant heads of the dental implants in association with FIG. 18D-2 below), the surgical guide section may be removed from the base frame 200, and corresponding implant components 1102 may be placed on the implants. Then, the transfer jig attachment 1104 can be placed on the base frame 200 letting the top of the implant components 1102 to go through its openings. If the transfer jig attachment is to be placed on the additional foundation superstructure, it needs to be attached to the base frame first. Furthermore, if a rubber gasket is used to protect the surgical site, it should be placed in-between the base frame and the transfer jig attachment 1104. Following this step, and with each implant component fully engaging a corresponding implant (e.g., an implant head 1303 by way of an attachment mechanism) the implant components 1102 can be fixated to the transfer jig 1104 with a dental adhesive or luting agent such as a light cured or self-curing composite material, a liquid and powder duralay material, and a resin type bonding material. A type of mechanical fixture may also be used for securing the implant components 1102. After the implant components are securely fixated to the transfer jig 1104, they can be detached from the implants and removed from the mouth with the transfer jig attachment 1104. Subsequently, the obtained physical positional index can be transferred to either the physical preoperative dental model 100 or to the digital preoperative model 100.

If the positional index of the installed implant or implants is to be transferred to the physical preoperative dental model 100 that was developed from the preoperative tomography scan and/or surface scan of the patient and manufactured by rapid prototyping, the transfer appliance and the base frame 200 and other associated foundation section (if any) can be transferred back onto the physical preoperative dental model 100. At first, the corresponding implant analogs or other corresponding parts that can be used to represent installed implants on the model are attached to the implant component 1102 fixated to the transfer appliance 1104 or 500. After some adjustment of the physical preoperative model 100, the appliance sections can be properly placed back on the model along with the impression components. Then, the implant analogs are fixated to the model 100 by traditional adhesive materials such as light cured or self-curing composites and duralay materials and they can be detached from the implant component 1102 still attached to the transfer appliance 1104 or 500, converting the preoperative model into a postoperative dental model. If necessary, additional postoperative information such as the contour of the healed gum tissue may be added to the model 100 using traditional lab procedures and various types of postoperative appliances and restorations can be made based on this postoperative dental model. The postoperative appliances and restorations includes but not limited to a implant verification jig, a try-in prosthesis, an implant bar, and a fixed or removable final restoration. This way, any other preoperative information indexed to the model 100 can be fully utilized. Other preoperative information may include but not be limited to the patient's duplicated existing denture, model of the natural dentition before extraction, model that includes old fixed or removable prosthesis, bite registration, and diagnostic prosthesis designed by a dental laboratory or a dental practitioner.

If the positional index of the installed implant or implants is to be transferred to the digital preoperative dental model 100, a surface scan of the transfer jig 1104, denture duplicate attachment appliance 500 or other transfer appliance along with the impression copings may be taken with a desk top or hand held scanner, and the scan data can be superimposed on the digital model 100 stored within the master data file by using a CAD software. By aligning the transfer appliance's image inside the new scan data to the design of the same appliance in the master data file, the partial image of implant components 1102 in the scan data can be positioned on the preoperative model 100. Then, by superimposing the commercially available digital designs or scanned image of the installed implants and/or corresponding implant components 1102, the digital preoperative dental model can be converted into the working postoperative model including locating the implants by way of implant components 1102. Similar to the method of using a physical diagnostic model 100, if other pieces of preoperative information are digitally stored in the master data file, they can also be utilized for designing of a new implant prosthesis as mentioned in the previous paragraph.

Figure 17:
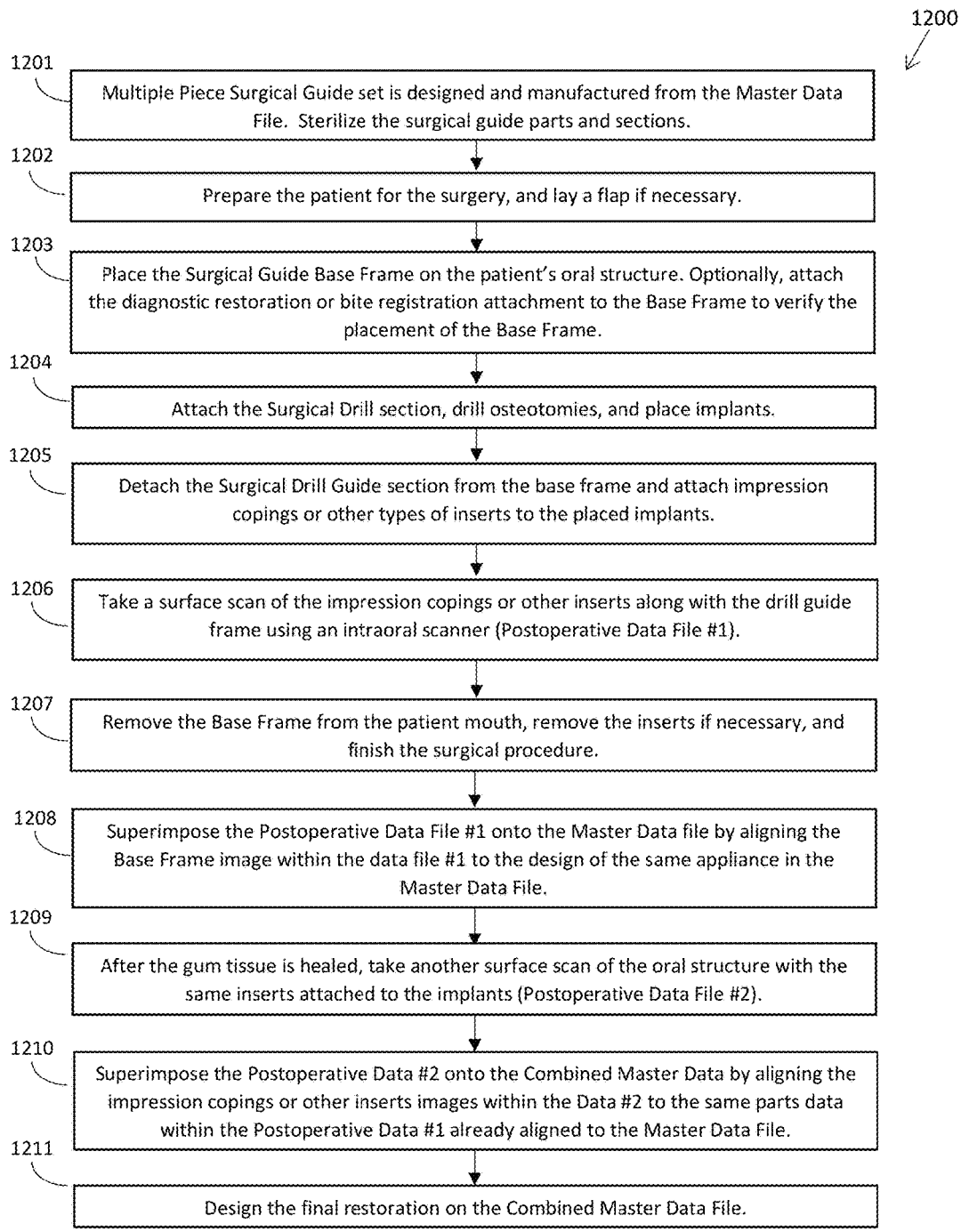
FIG. 17 is a diagram of how to utilize the multiple piece surgical guide set to take a digital dental impression and transfer the information back to the original master data file in order to design a new implant restoration.

FIG. 17 illustrates a flowchart 1200 of how the multiple piece surgical guide set 401, particularly the base frame 200, can be utilized during the surgery for taking a digital index of installed implants, and FIGS. 18A-F represent different steps of the flowchart 1200 to visualize the process using one exemplary implant placement surgery of a lower jaw. It will be appreciated that the steps shown in FIG. 17 can be modified depending on each patient's condition or the preference of the dental practitioner, yet remains within the spirit of the exemplary illustrations herein. It should be noted that the chart in FIG. 17 is not intended to teach the surgical procedure itself. Additionally, although the surgery exemplified in FIG. 17 and FIG. 18A-G describe and illustrate a flap surgery with placement of multiple implants, the same basic process can be followed even if it is to be a flapless surgery or a surgery with only one implant placement. For an easy workflow, the surgical guide sections should be digitally designed on the digital dental anatomical diagnostic model 100 representing a preoperative digital dental model, which may be developed from at least one of a tomography scan data, topography scan data of the patient's oral structure, digital topography data of the patient's dental impression, or digital topography data of the patient's existing removable dental prosthesis with or without modification, and stored within the master data file. The master data file may include one or more of the patient's other preoperative information having coordinates in relation to the preoperative digital dental model 100 (step 1201, FIG. 17). Such information may include but not limited to the tomography and/or surface scan data of surface scan of natural dentition before extraction, diagnostic prosthesis, bite registration, and opposing oral structure. It should also be noted that the base frame of the multiple piece surgical guide set 401 can be designed as bone-borne appliance, bone and mucosa borne appliance, or mucosa borne appliance.

The surgical guide set may also fit to the remaining existing dentition or artificial fixed prosthesis if any.

Figure 18A:
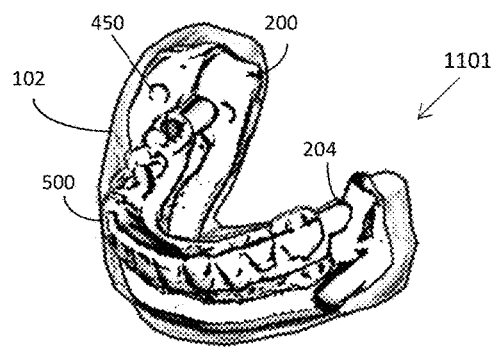
FIG. 18A is a perspective view of an illustrative modified duplicated denture attachment or temporary denture restoration attached to the base frame of a multi-piece edentulous surgical guide set which is placed on the lower jaw of a patient.

Prior to the surgery, all the parts of the drill guide set 401 are properly sterilized according to the material's requirement just as is explained in FIG. 15, step 1001. Prepare the patient for the surgery, and lay a flap if necessary (step 1202, FIG. 17). Place the surgical guide base frame 200 on the patient's oral structure. If a modified duplicated denture attachment 500 and/or bite registration attachment is created, the base frame 200 can be positioned using one or more of those superstructures (step 1203). If desired, the base frame can be secured to the patient's oral structure using one or more anchor screws or pins. FIG. 18A illustrates an exemplary modified duplicated denture attachment 500 attached to the base frame 200. It should be noted that, although the modified duplicated denture attachment 500 was introduced as a simulated diagnostic prosthesis modeled after the patient existing denture, it may also be modeled after other types of existing prosthesis, a diagnostic prosthesis design, or the patient's natural dentition. Though it is not illustrated, the duplicated denture attachment 500 may also be positioned on the surgical drill guide section 400 or any other superstructure placed on the base frame 200.

Figure 18B:
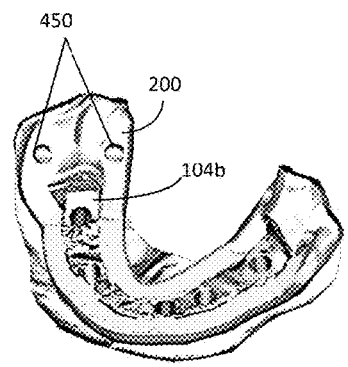
FIG. 18B is a perspective view of the base frame/Bone Reduction Jig on the patient's jaw with exposed bone after bone adjustment.
Figure 18C:
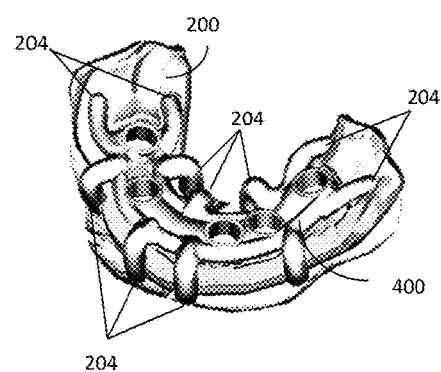
FIG. 18C is a perspective view of the surgical drill guide section attached to the base frame of the multiple piece surgical guide set on the patient lower jaw.

After the base frame 200 is properly and securely positioned in the patient's oral structure, the superstructure that was used for positioning can be removed. If desired, the jaw bone can be adjusted using the base frame as a bone reduction jig as shown in FIG. 18B. Then, the surgical drill guide section 400 may be attached to the base frame 200 as shown in FIG. 18C, osteotomies are drilled, and implants are placed (step 1204). Although it may be desirable under some circumstances to use a surgical drill guide section 400 for drilling osteotomies, if the multiple piece surgical guide set 401 is made just to get a rough idea of desirable implant locations and to take a postoperative positional index of installed implants, the surgeon may use the base frame 200 and duplicated denture attachment as approximate guides and drill osteotomies without a surgical drill guide section 400.

Figures 1, 18D:
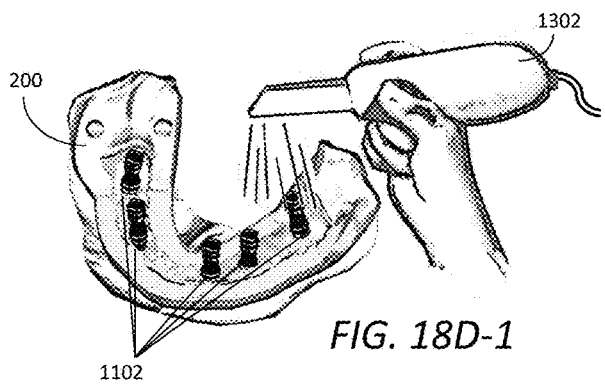
Figures 2, 18D:
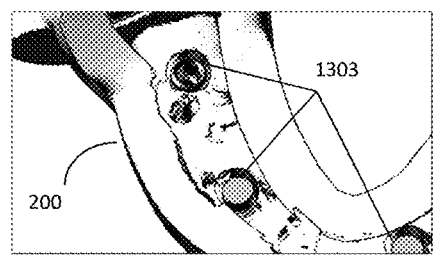
Figures 1, 18E:
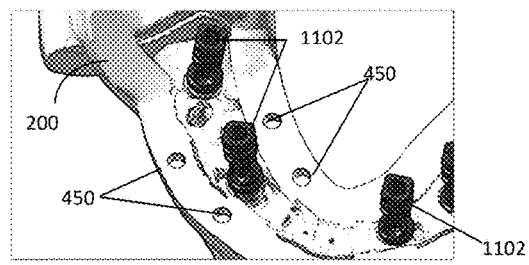
Figures 2, 18E:
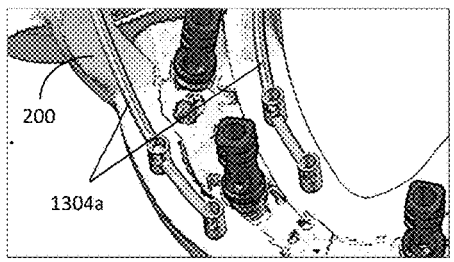
Figures 3, 18E:
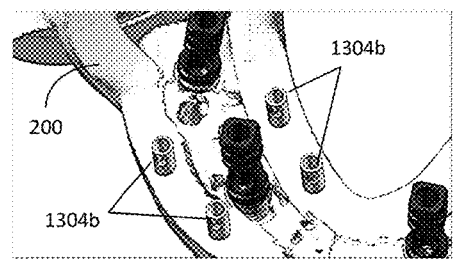

Following this process, the surgical guide section 400 (if used) can be detached from the base frame 400, and corresponding implant components 1102 such as a scan body, impression coping, temporary implant abutment and other types of components that are securely and repeatedly attachable to the particular implants may be attached to the installed implants (step 1205). Then, the base frame 400 can be used as a fiducial marker/scan appliance. Utilizing an intraoral scanner 1302 as shown in FIG. 18D-1, a surface scan of the implant components/scan bodies 1102 placed on the installed implants (e.g., implant heads 1303 as shown in FIG. 18D-2) are taken along with the base frame 200 still placed on the patient oral structure as a fiducial marker. This creates a digital impression of the patient mouth with a positional index of the installed implants. Although another type of superstructure 1304*a* (exemplified in FIG. 18E-2) or multiple pieces of a smaller attachment 1304*b* (exemplified in FIG. 18E-3) can be attached to the base frame 200 with some type of alignment member(s) 450 (FIG. 18E-1) and used as a fiducial marker or a part of fiducial marker, it is important that the appliance has a large enough opening around the surgical site so that the clear optical view of the implant components/scan bodies 1102 can be obtained when a digital impression is taken. This creates the first 'postoperative data file' (step 1206). It should be noted that, a surface scan may be taken without scan components/scan bodies 1102, if the implants (e.g., heads 1303 as shown in FIG. 18D-2) are visible above the surface of the oral structure of a patient mouth and provide enough informational points in order to determine the position and orientation of the installed implants. Additionally, the base frame 200 may be removed from the patient's oral structure and placed back in position during and after the surgery before the scan is taken.

Please appreciate that by either capturing the three-dimensional coordinates of the implants directly or indirectly (e.g., by fixing implant components 1102 to the implants including implant heads 1303) a fixed position in three dimensions is provided of the various elements that may ultimately be captured and stored in the master data file by combining the preoperative data in the master data file with data added by way of one or more postoperative data scans. Elements that are common between the various scans such as elements of the surgical guide including base frame 200 or some other fixed and constant reference marker (e.g., the implant location represented by an implant head once surgery takes place which will be a reference marker for subsequent postoperative scans) provide the necessary frame of reference so that the various data scans may be aligned with the elements positioned in three-dimensional space by way of coordinates in a proper orientation with respect to other elements even if those elements only exist in at most one of the scans. A reference marker must be same between at least two sequential scans For example, a first reference marker may exist between a preoperative scan and a postoperative scan. In this example, a second reference marker may then exist between the initial postoperative scan and a further postoperative scan (e.g., after tissue healing). Because two reference markers exist in the second scan, the coordinates of the first scan and the third scan may also be linked together. Data from all of the scans must be able to be superimposed and aligned and the reference markers provide consistent or common points of reference.

Figure 18F:
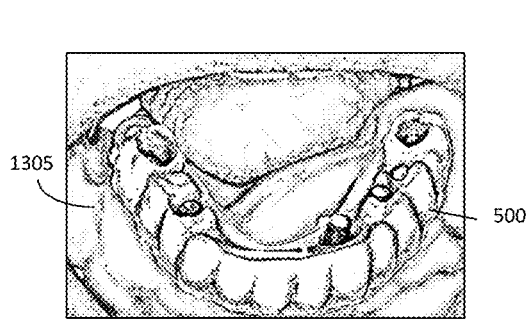
FIG. 18F is a patient's mouth with a temporary prosthesis ready to receive the connective implant components.

After the first digital impression is taken, the base frame 200 and the implant components/scan bodies 1102 can be removed if the surgeon choses to suture up the gum tissue and bury the implants for integration as a majority of implant surgeries are being done. Then, the surgeon may move on to finishing up the surgery. However, if the surgeon chooses the immediate loading implant procedure, a pre-fabricated temporary restoration such as a temporary prosthesis 500 can be positioned in mouth to be fixated to the implant components/scan bodies 1120. For easy positioning of the prosthesis, it may be designed as a superstructure of the guide set 1101 indexed to fit the base frame 200 and/or another superstructure such as an intermediate support frame or a surgical guide section 400. In that case, the base frame and the implant components/scan bodies will remain in the mouth to receive the temporary restoration and another superstructure. In one illustrative approach, a pre-fabricated rubber or silicon dam/separator 1305 is placed over the surgical sites below the temporary prosthesis for protection while the prosthesis is being prepared as shown in FIG. 18F. In the particular case shown in FIG. 18A-G, the duplicated modified denture attachment 500 is also being used as the temporary prosthesis. If the temporary prosthesis/duplicated modified denture attachment 500 is to be positioned on top of the base frame 200, the rubber dam/separator 1305 should have openings not only for the implant components but also for accommodating the connectors to the base frame. Additionally, this rubber dam/separator 1305 may be designed as another superstructure that is indexed to fit between the temporary prosthesis 500 and the base frame 200. After the impression copings or temporary abutments are attached to the temporary prosthesis, the surgeon will make necessary adjustment, and complete the surgery process (step 1207).

Meanwhile, the first 'postoperative data' created by taking a digital impression can be transferred to the combined master data file and superimposed onto the original digital master model by aligning the partial image of the base frame 200 and/or the superstructure captured in the scan image with the design of the same surgical guide section(s) on the digital master dental. The image of the scan components/scan bodies 1102 or the implants themselves such as implant heads 1303 if they can be directly scanned will be oriented to the digital preoperative digital model 100 as well since it is a part of this scan data. Then, by using the commercially available digital designs or scanned image of the installed implants and/or corresponding components, the actual positions of the installed implants can be digitally recorded on the digital preoperative dental model 100, easily updating converting the model into the postoperative model even if the gum tissue contour is drastically changed. With certain types of implant components/scan bodies 1102, it may not be even necessary to do this extra alignment with the design(s) of implant components to create the working digital postoperative model (step 1208). If the combined master data file contains other important preoperative information, which may include but not limited to the old denture or other fixed or removal prosthesis, old natural dentition, diagnostic restoration design, midline, bite registration, articulation to the opposing jaw, oriented to the digital preoperative dental model, the first step for creating a new prosthesis can be immediately started without obtaining such information again.

Figure 18G:
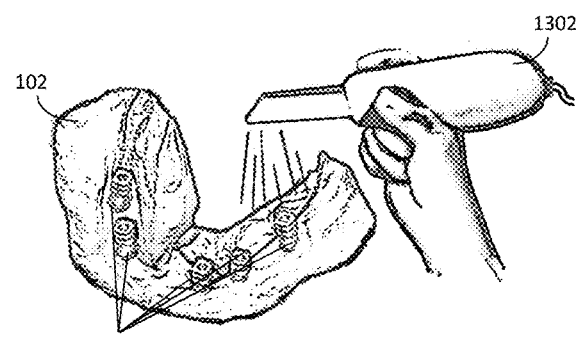
FIG. 18G is a simplified drawing of an intraoral scanner taking a digital impression of the patient's lower jaw with implant components attached on the installed implants after the gum tissue is properly healed.

As illustrated in FIG. 18G, after the gum tissue is healed and implants are integrated, a new digital impression may be taken with an intraoral scanner 1302 to capture the record of the new gum tissue contour in relation to the installed implants (step 1209). If the corresponding implant components/scan bodies 1102 were placed on the implants when the first digital impression was taken, the following types of components may be used for the second scan: (1) the components that have same shape as the ones used for the first digital impression, (2) the different types of components which correspond to the particular implants used in the surgery and their digital designs are available within the CAD software program and interchangeable with the original components. This process will create the second 'postoperative data file'.

Followed by this process, the second scan data (the second digital impression) may be transferred to the combined master data file and aligned with the new digital master dental model, this time, using the image of the implant components/scan bodies (in this case the temporary prosthesis is also the duplicated modified denture attachment 500) 1102, or the implant heads 1303 as fiducial markers to be matched with the same parts of the first 'postoperative data' already aligned to the digital master dental model (step 1210). Since these impression copings 1102 or other implant components are provided with optical recognition points that can be used for photogrammetric determination of the orientation and position and these recognitions points have predetermined position relative to the matching implants (U.S. Pat. No. 5,857,853 to W. F. van Nifterick, et. al is incorporated by reference herein), this series of new scan data will provide enough information to the new master dental model for creating a new fixed or removable implant prosthesis and related parts as previously described. A new implant prosthesis may be designed on the digital master dental model utilizing a CAD software program.

Alternatively, a new physical master dental model may be manufactured by rapid prototyping, and the prosthesis may be created by a more traditional method.

Additionally, by using a base frame 200 while taking an intraoral scan, any distortion that may occur in the scan image can be corrected when it is aligned to the digital design of the base frame. In spite of recent technological improvement of intraoral scanners and excellent accuracy in their single unit scans, multiple studies still find that the accuracy of intraoral scanners in full arch scan still trails behind that of conventional dental casts (see by way of example, Sebastian B M Patzelt et al. 'Accuracy of full-arch scans using intraoral scanners' Clin Oral Investig. 2014 Jul. 17; 18(6):1687-94. Epub 2013 Nov. 17).

FIGS. 19A and 19B illustrate a perspective view and a top view of a patient mouth after installation of implants with another exemplary base frame 200 positioned on the patient's gum tissue and fixated by fixation pins 1401 and implant component/scan bodies 1102 attached to each installed implant. Since intraoral scanners can take a scan of small area at a time, series of sectional scans are taken as the user move a scanner along the arch of a patient's mouth, and those sectional scans are digitally stitched together to create a full arch scan of the patient's mouth. FIG. 19C is an exaggerated illustration showing how small sections of intraoral scan image 1402 of the patient mouth can be digitally combined and small error in each section may result in substantial inaccuracies in a full arch scan data. However, if the scan is taken with a digitally designed and manufactured base frame, these inaccuracies are correctable by superimposing the images and corresponding coordinates and then aligning the coordinates from the scanned image (FIG. 19C) onto the corresponding coordinates from digital design of the base frame 200 designed on the digital preoperative dental model 100 shown in FIG. 19D using an appropriate computer software program as shown in FIG. 19E. Thus, scan image of implant components 1102 can be placed in correct coordinates with the digital preoperative model 100 creating an accurate postoperative digital master model 1403. It should be also noted that a dental practitioner may place implants and take a digital positional index just by utilizing a base frame as the only guide appliance without any superstructures basically following the flowchart 1200.

As discussed above, one key advantage is that, by utilizing at least one section of the multiple piece surgical guide set 401, the critical pieces of preoperative information can be easily retained even if the contour of the patient's oral structure is drastically changed from the preoperative contour because it is usually much more technically difficult and cumbersome to obtain some of this information that are essential in order to create a new prosthesis. Consequently, this approach spares the dental practitioners and laboratory technicians from recapturing of such pieces of information and/or making numerous adjustments back and forth between these dental professionals and make the process much easier and quicker.

Figure 20A:
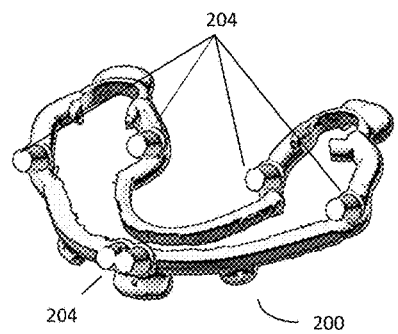
FIG. 20A is a perspective view of another exemplary base frame with horizontal interlocking connectors.
Figure 20B:
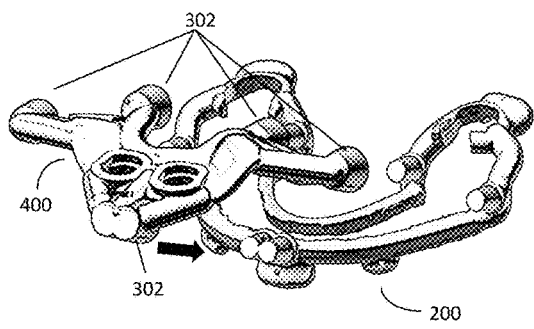
FIG. 20B is an illustration showing how another exemplary surgical guide superstructure with horizontal connector receptors is being attached to a base frame.
Figure 20C:
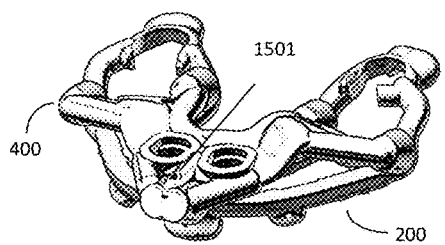
FIG. 20C is a perspective view of an exemplary surgical guide superstructure attached to a base frame.
Figure 20D:
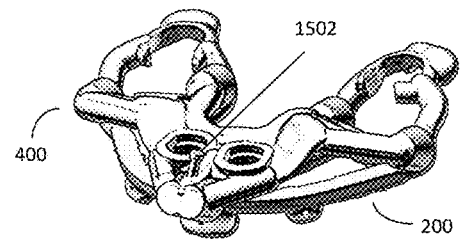
FIG. 20D is a perspective view of an exemplary surgical guide superstructure attached to a base frame and fixated with a locking pin.
Figure 20E:
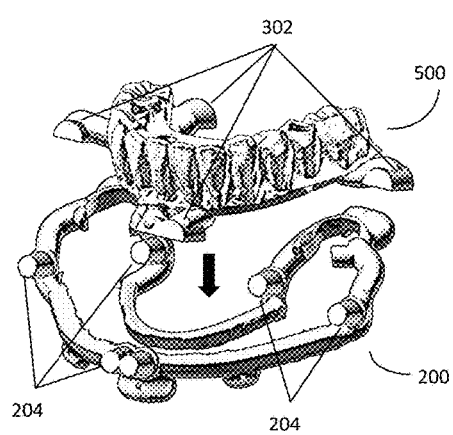
FIG. 20E is an illustration showing how another exemplary modified duplicated denture attachment with vertical connector receptors is being positioned on horizontal connectors of a base frame.
Figure 20F:
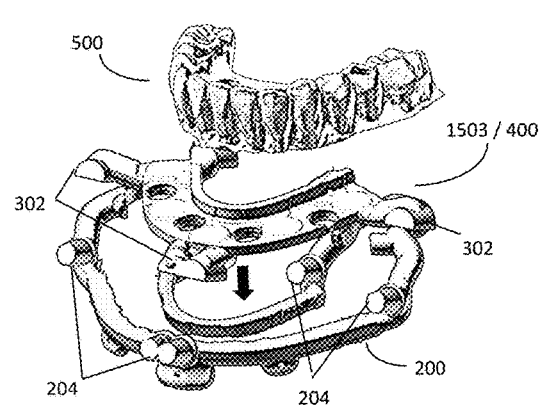
FIG. 20F is an illustration showing how an exemplary multi-piece modified denture attachment set is being positioned on horizontal connectors of a base frame.
Figure 21A:
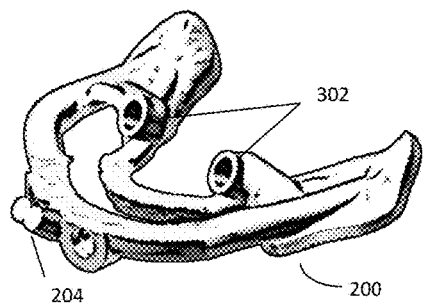
FIG. 21A is a perspective view of another exemplary base frame with a horizontal interlocking connector and horizontal connector receptors.
Figure 21B:
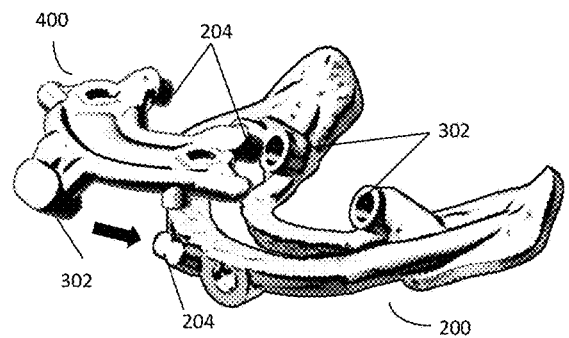
FIG. 21B is an illustration showing how another exemplary surgical guide superstructure with horizontal connectors and a connector receptor is being attached to a base frame.
Figure 21C:
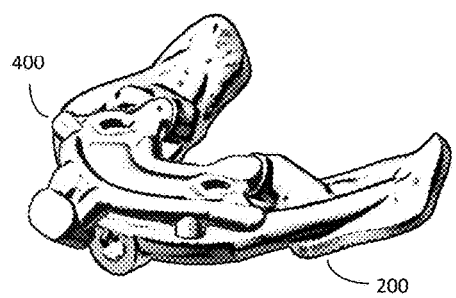
FIG. 21C is a perspective view of an exemplary surgical guide superstructure attached to a base frame.
Figure 21D:
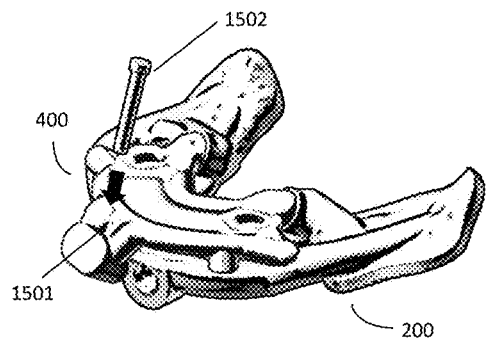
FIG. 21D is an illustration showing how a locking pin is being inserted into receiving holes of a surgical guide superstructure and a base frame.
Figure 21E:
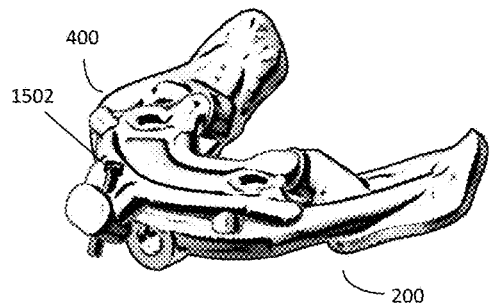
FIG. 21E is a perspective view of an exemplary surgical guide superstructure attached to a base frame and fixated with a locking pin.
Figure 21F:
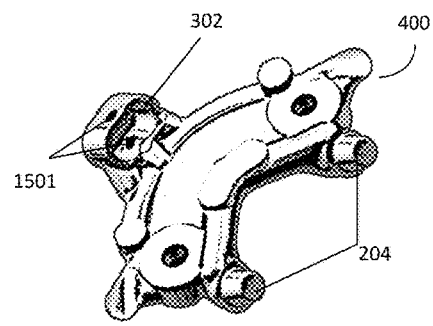
FIG. 21F is a bottom view of an exemplary surgical guide superstructure.

As previously mentioned, various types of superstructures are detachably attachable to a base frame 200 by means of various types of connecting members and alignment members. FIG. 20A-F and FIG. 21A-F illustrate different examples of base frames 200 and superstructures, which comprise horizontal slide-in type connectors 204. FIG. 20A shows an exemplary base frame 200 with horizontal slide-in type male connectors 204 and FIG. 21A shows another exemplary base frame 200 with a same type male connector and slide-in type connector receptors. FIG. 20B and FIG. 21B illustrate how exemplary surgical guide housing sections 400 in the form of superstructures that comprise horizontal connector receptors 302 and/or slide-type male connectors 204 are being attached to the base frame 200 with corresponding connecting members and FIG. 20C and FIG. 21C are perspective views of surgical guide superstructures 400 positioned properly on the corresponding base frames 200. With horizontal connectors 204, a surgical guide superstructure can be attached to the base frame in a generally horizontal slide-in motion though the connectors and receptors may be slightly tilted, as shown in FIGS. 21 and 22, for ease of use. The horizontal slide-in connectors 204 have benefit of preventing the surgical guide superstructure 400 from snapping off of the base frame 200 despite of the fact that the torque from drilling for implants causes force to lift the surgical guide 400 away from the jaw bone. A slide-in connector 204 and a connector receptor 302 may have a snap-lock function. If they do not have a snap-lock function, a locking pin 1502 may be used instead. As shown in FIG. 20D, FIG. 21D and FIG. 21E, a locking pin 1502 is inserted into reception holes 1501 through a base frame 200 and also a surgical drill guide superstructure 400 to keep the surgical drill guide section from sliding. FIG. 21F is a bottom view of the surgical drill guide exemplified in FIG. 21A-E and it shows reception holes on the top and bottom walls of the connector receptor.

A horizontal slide-in connector 204 may also be used as a vertical connector 204 by another superstructure. A single-piece modified duplicated denture attachment 500 shown in FIG. 20E and a denture attachment base tray 1503 of a multi-piece denture attachment 500 shown in FIG. 20F have connection receptors 302 that vertically fit onto the horizontal connectors 204 of the corresponding base frames 200.

Figure 22A:
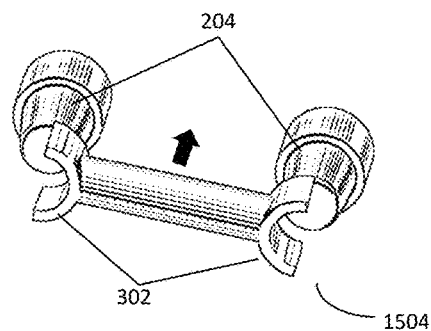
FIG. 22A is an illustration showing how an exemplary connecting mechanism works.
Figure 22B:
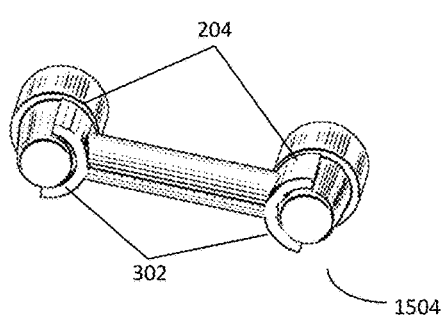
FIG. 22B is an illustration of exemplary horizontal connectors and connector receptors connected together.
Figure 23A:
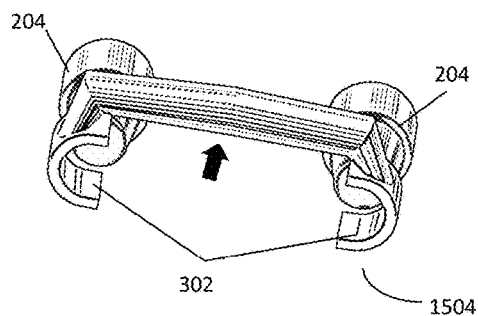
FIG. 23A is an illustration showing how another exemplary connecting mechanism works.
Figure 23B:
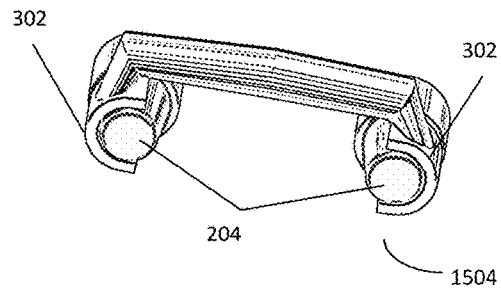
FIG. 23B is an illustration of exemplary horizontal connectors and another exemplary connector receptors connected together.

It should be noted that different types of connecting members and/or alignment members may be used to support different superstructures on one multiple piece stackable surgical drill guide set. FIG. 22A-B and FIG. 22A-B illustrate other variations of connecting mechanisms with horizontal type of connectors 204, which can be incorporated into a base frame 200 and superstructures such as a surgical guide superstructure 400. As shown in these figures, connector receptors 302 may not be encircled tubes and may work with another set of a connector 204 and a receptor 302 to connect a superstructure to a base frame or to another superstructure. Although it is not shown a horizontal slide-in connector may be wider and take a shape of a wall and a slit or a shelf.

What is claimed is:

1. A method comprising:
receiving a digitally stored scan of a preoperative dental model including preoperative scan coordinates of at least a subset of at least one of a tomography of an oral structure of a patient, a topography of the oral structure, a dental impression of the oral structure, and a removable prosthesis of the patient as applied to the oral structure;
designing digitally a guide appliance with design coordinates using the preoperative dental model, the guide appliance comprising at least one opening configured to provide a view of a surgical site on the oral structure;
storing the design coordinates of the guide appliance as part of the preoperative dental model;
receiving a digitally stored postoperative scan including postoperative scan coordinates of at least a subset of a physical representation of the guide appliance manufactured using the design coordinates positioned on the oral structure and at least a portion of at least one of (i) an installed implant installed at the surgical site and (ii)

an implant component associated with the installed implant, thereby locating the at least one implant in the postoperative scan;

superimposing the postoperative scan coordinates onto the preoperative dental model represented by the preoperative scan coordinates; and aligning common coordinates of at least the guide appliance stored as part of the preoperative dental model and the postoperative scan, thereby forming a postoperative dental model including the location of the at least one implant.

2. The method of claim 1, wherein the common coordinates include a fixed and constant reference marker whose coordinates are consistent and do not change between each of the scannings.

3. The method of claim 1, further comprising:
a digitally stored second postoperative scan including second postoperative scan coordinates of at least one of at least a portion of (i) the installed implant, (ii) a scan body, which may selectively include the implant component associated with the postoperative dental model, and (iii) the oral structure, for locating the at least one implant;
and
superimposing the second postoperative scan coordinates onto the postoperative scan coordinates of the postoperative dental model and forming a healed postoperative dental model.

4. The method of claim 1, wherein the guide appliance includes a base frame of a multi-piece stackable surgical guide set and a surgical drill guide attached to the base frame.

5. The method of claim 3, further designing, storing, and manufacturing an implant verification jig using the postoperative model, the implant verification jig acting as the scan body.

6. The method of claim 1, wherein errors from said postoperative scan may be corrected by superimposing the postoperative scan coordinates of the guide appliance onto the design coordinates of the guide appliance and aligning the corresponding coordinates to remove the errors.

7. The method of claim 1, the preoperative dental model including coordinates representing a subset of a patient's existing denture, natural dentition before extraction, existing partial denture, bite registration, opposing oral structure, and a diagnostic prosthesis designed prior to the surgery.

8. The method of claim 1, the preoperative dental model further including an existing denture, a model of a natural dentition before extraction, a prosthesis, a bite registration, and a diagnostic prosthesis.

9. The method of claim 1, comprising:
designing digitally a proposed prosthesis with design coordinates using the preoperative dental model; and
storing the design coordinates of the proposed prosthesis as part of the preoperative dental model.

10. A method comprising:
receiving a digitally stored scan of a preoperative dental model including preoperative scan coordinates of at least a portion of an oral structure having at least one surgical site;
designing digitally in the preoperative dental model a guide appliance engaging at least a portion of the oral structure;
capturing a fixed and constant reference marker from at least one of the preoperative scan coordinates and the guide appliance, the reference marker being stored within the preoperative dental model;

receiving a digitally stored postoperative scan including postoperative scan coordinates of at least a subset of a physical representation of the guide appliance guide appliance placed on the oral structure and at least one of a portion of an installed implant and any corresponding implant component associated with the installed implant, thereby locating the at least one implant in the postoperative scan, the postoperative scan further capturing the fixed and constant reference marker;

superimposing the postoperative scan coordinates onto the preoperative digital dental model; and aligning common coordinates from the preoperative dental model and the postoperative scan by way of the fixed and constant reference marker, thereby forming a postoperative dental model including the location of the at least one implant.

11. The method of claim 10, wherein the guide appliance includes a base frame of a multi-piece stackable surgical guide set and a surgical drill guide attached to the base frame.

12. The method of claim 10, further comprising:
a digitally stored second postoperative scan including second postoperative scan coordinates of at least one of at least a portion of (i) the oral structure, (ii) the installed implant, and (iii) a scan body, which may selectively include the implant component associated with the postoperative dental model, and locating the at least one implant;
and
superimposing the second postoperative scan coordinates onto the postoperative digital dental model and forming a healed postoperative dental model using common coordinates including the location of the at least one implant.

13. The method of claim 12, wherein errors from the second postoperative scan may be corrected by superimposing the second postoperative scan coordinates representing at least a portion of of the guide appliance from the second postoperative scan onto coordinates representing the portion of the guide appliance in the preoperative dental model and aligning the corresponding coordinates to remove the errors.

14. The method of claim 10, the preoperative dental model including coordinates for the guide appliance and coordinates representing a subset of a patient's existing denture, natural dentition before extraction, existing partial denture, bite registration, opposing oral structure, and a diagnostic prosthesis designed prior to the surgery.

15. The method of claim 10, comprising:
designing digitally a proposed prosthesis with design coordinates using the preoperative dental model; and
storing the design coordinates of the proposed prosthesis as part of the preoperative dental model.

16. The method of claim 12, further designing, storing, and manufacturing an implant verification jig using the postoperative model, the implant verification jig acting as the scan body.

17. A method comprising;
receiving a digitally stored scan of a preoperative dental model including preoperative scan coordinates of at least one of a tomography of an oral structure of a patient, a topography of the oral structure, a dental impression of the oral structure, and a removable prosthesis of the patient as applied to the oral structure;
designing digitally a guide appliance with design coordinates using the preoperative dental model, the guide appliance including a base frame and a superstructure including a transfer appliance indexed to the base frame, and comprising at least one opening configured to provide a view of a surgical site on the oral structure;

storing the design coordinates of the guide appliance as part of the preoperative dental model;

receiving a digitally stored postoperative scan including postoperative scan coordinates of a physical representation of at least a portion of the guide appliance and a fixed implant component of at least one implant, wherein a first portion of the implant component selectively engages the at least one implant and a second portion of the implant component selectively engages the at least one transfer appliance of the guide appliance;

superimposing the postoperative scan coordinates onto the preoperative digital dental model represented by the preoperative scan coordinates; and aligning common coordinates of the preoperative scan coordinates and the postoperative scan coordinates, thereby forming a postoperative dental model including the location of the at least one implant.

18. The method of claim 17, wherein the common coordinates include a fixed and constant reference marker whose coordinates are consistent and do not change between each of the scanning.

19. The method of claim 17, the preoperative dental model including coordinates for the guide appliance and coordinates representing a subset of a patient's existing denture, natural dentition before extraction, existing partial denture, bite registration, opposing oral structure, and a diagnostic prosthesis designed prior to the surgery.

* * * * *